(12) United States Patent
Leschinsky et al.

(10) Patent No.: US 9,204,807 B2
(45) Date of Patent: Dec. 8, 2015

(54) DEVICES FOR NON-CONTACT THERMOGRAPHIC MAPPING OF TISSUE FOR VIABILITY ASSESSMENT AND METHODS OF THEIR USE

(71) Applicant: EMPIRE TECHNOLOGY DEVELOPMENT LLC, Wilmington, DE (US)

(72) Inventors: Boris Leschinsky, Mahwah, NJ (US); Jonathan Williams, Montville, NJ (US); Robert B. Schock, Sparta, NJ (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 150 days.

(21) Appl. No.: 14/006,801

(22) PCT Filed: Feb. 15, 2013

(86) PCT No.: PCT/US2013/026338
§ 371 (c)(1),
(2) Date: Sep. 23, 2013

(87) PCT Pub. No.: WO2014/126581
PCT Pub. Date: Aug. 21, 2014

(65) Prior Publication Data
US 2014/0236020 A1     Aug. 21, 2014

(51) Int. Cl.
*A61B 5/00* (2006.01)
*A61B 5/01* (2006.01)

(52) U.S. Cl.
CPC ............... *A61B 5/015* (2013.01); *A61B 5/0075* (2013.01)

(58) Field of Classification Search
CPC ...... A61B 5/483; A61B 5/015; A61B 5/0077; A61B 5/0075; A61B 5/7282
See application file for complete search history.

(56) References Cited

U.S. PATENT DOCUMENTS

| | | | |
|---|---|---|---|
| 5,800,350 | A | 9/1998 | Coppleson et al. |
| 6,450,971 | B1 | 9/2002 | Andrus et al. |
| 2006/0100489 | A1 | 5/2006 | Pesach et al. |
| 2007/0225614 | A1 | 9/2007 | Naghavi et al. |
| 2008/0111078 | A1 | 5/2008 | Sun |
| 2009/0259139 | A1 | 10/2009 | Stepien et al. |

(Continued)

OTHER PUBLICATIONS

International Search Report and Written Opinion for PCT/US2013/026338 dated Jun. 18, 2013.

(Continued)

*Primary Examiner* — Michael Rozanski
(74) *Attorney, Agent, or Firm* — Foley & Lardner LLP

(57) ABSTRACT

Systems and methods for remote thermographic assessment of tissue viability are disclosed. A system may include a controllable source of one or more thermal stimuli to be applied to a tissue, a measurement system to measure a heat response of the tissue before, during, and/or after the application of the thermal stimuli, and an electronic device that may control either one or both of the source of thermal stimuli and the measurement system. The electronic device may also receive tissue thermal response data from the measurement system, and may further calculate a measure of tissue viability. A method of determining tissue viability may include supplying a thermal stimulus to a tissue, receiving, by a measurement device, the thermal response of the tissue to the stimuli, and a comparison of the thermal response data to at least some viability threshold values. The results may be displayed in a graphical manner.

34 Claims, 12 Drawing Sheets

(56) References Cited

U.S. PATENT DOCUMENTS

| | | |
|---|---|---|
| 2010/0081893 A1 | 4/2010 | Jarvik et al. |
| 2010/0249532 A1 | 9/2010 | Maddesi et al. |
| 2011/0028804 A1 | 2/2011 | Jernigan |
| 2011/0224518 A1 | 9/2011 | Tindi et al. |

OTHER PUBLICATIONS

Arkin et al., Thermal Pulse Decay Method for Simultaneous Measurement of Local Thermal Conductivity and Blood Perfusion: A Theoretical Analysis, *Journal of Biomechanical Engineering* (Aug. 1, 1986), 108(3):208-214 (Abstract).

Berz et al., The Medical Use of Infrared-Thermography History and Recent Applications, *Thermografie-Kolloquium* (2007) 4:1-12.

Brooks et al., Thermal imaging in the detection of bowel ischemia, *Diseases of the Colon & Rectum* (Sep. 2000), 43(9):1319-1321 (Abstract).

Chato, A method for the measurement of the thermal properties of biological materials, *American Society of Mechanical Engineers* (Jan. 1, 1968) (Abstract).

Dickey et al., Burn-depth estimation using thermal excitation and imaging, *Proc. SPIE, Biomedical Diagnostic, Guidance, and Surgical-Assist Systems* (Jul. 9, 1999), vol. 3595 (Abstract).

Jones, A reappraisal of the use of infrared thermal image analysis in medicine, *Medical Imaging, IEEE Transactions* (Dec. 1998), 17(6):1019-1027 (Abstract).

Junila et al., Assessment of tissue viability by thermography after experimentally produced frostbite of the rabbit ear, *Acta Radiol.* (Nov. 1993), 34(6):622-624 (Abstract).

Kaczmarek et al., Thermal monitoring of the myocardium under blood arrest preliminary study, *29$^{th}$ Annual International Conference of the IEEE* (Aug. 22-26, 2007), pp. 254-257 (Abstract).

Liu et al., Sinusoidal heating method to noninvasively measure tissue perfusion, *IEEE Trans Biomed Eng.* (Aug. 7, 2002), 49(8):567-877 (Abstract).

Malafaia et al., Infrared imaging contribution for intestinal ischemia detection in wound hearling, *Acta Cir Bras.* (2008), 23(6):511-519.

Miland et al., Intraoperative use of dynamic infrared thermography and indocyanine green fluorescence video angiography to predict partial skin flap loss, *Eur J Plast Surg.* (2007), pp. 1-8.

Moderhak et al., The influence of carbon dioxide on dynamic thermography results, *10$^{th}$ International Conference on Quantitative Infrared Thermography* (Jul. 27-30, 2010), pp. 1-2.

Moss et al., Use of Thermography to Predict Intestinal Viability and Survival After Ischemic Injury: A Blind Experimental Study, *Invest Radiol* (1981), 16(1):24-29 (Abstract).

Nishikawa et al., Intraoperative Thermal Imaging in Esophageal Replacement: Its Use in the Assessment of Gastric Tube Viability, *Surgery Today* (Sep. 2006), 36(9):802-806 (Abstract).

Roberts et al., Laparoscopic infrared imaging, *Surgical Endoscopy* (Dec. 1997), 11(12):1221-1223 (Abstract).

Urbanavičius et al., How to access intestinal viability during surgery: A review of techniques, *World J Gastrointest Surg.* (May 27, 2011), 3(5):59-69.

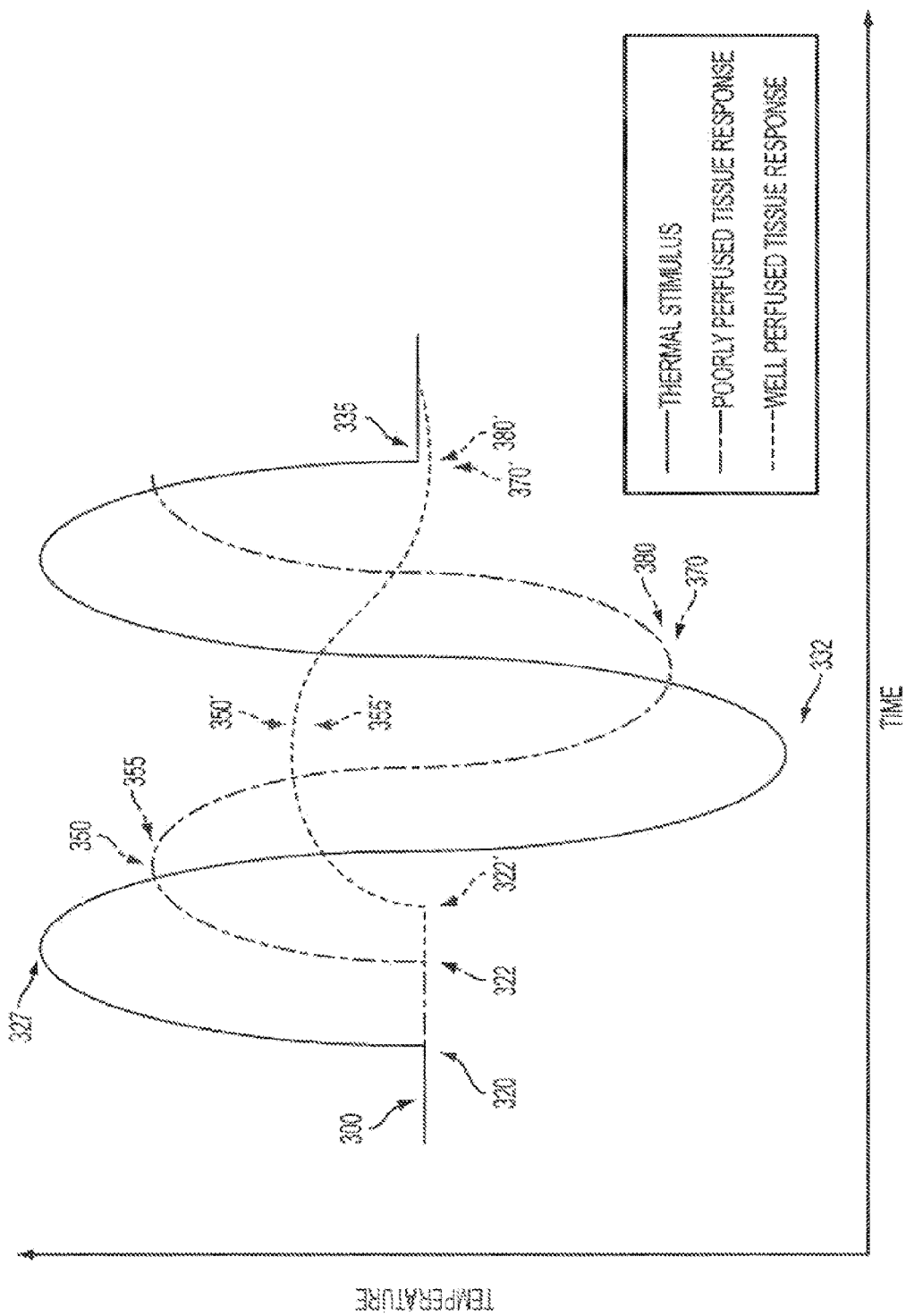

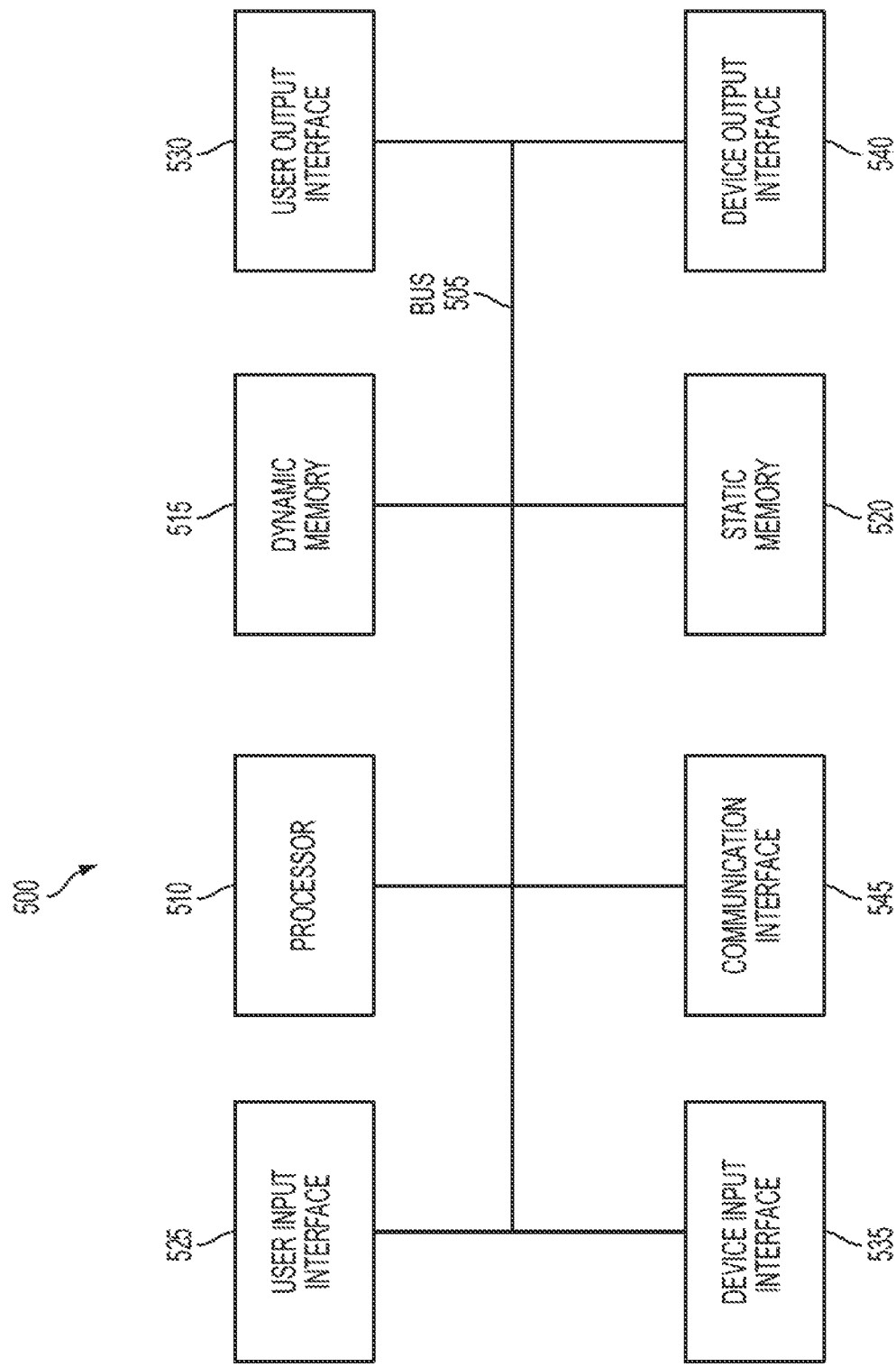

US 9,204,807 B2

DEVICES FOR NON-CONTACT THERMOGRAPHIC MAPPING OF TISSUE FOR VIABILITY ASSESSMENT AND METHODS OF THEIR USE

CROSS-REFERENCE TO RELATED APPLICATIONS

This application is a U.S. national stage filing under 35 U.S.C. §371 of International Application No. PCT/US2013/026338 filed Feb. 15, 2013 and entitled "Devices for Non-Contact Thermographic Mapping of Tissue for Viability Assessment and Methods of Their Use," the disclosure of which is incorporated by reference in its entirety.

BACKGROUND

Hundreds of thousands of colorectal surgeries are performed every year to resect a diseased portion of the bowel or intestines. Such resection may necessitate an anastomotic connection between the remaining portions of the bowel and/or intestine. Surgical success may depend on several factors, including tissue viability around the anastomotic connection.

Bowel tissue may be highly sensitive to ischemia. Sufficient blood supply is highly important for successful healing of the anastomosis and avoidance of intestinal ischemia and necrosis. Insufficient microcirculation of the anastomotic region may lead to anastomotic leakage. Such anastomotic leakage may result in an increased length of hospital stay, significant postoperative morbidity and mortality, and tumor recurrence after resections for malignant tumors. The reported incidence of anastomotic leakage may be as high as 20%. According to some statistics, up to 50% of patients with an anastomotic leak die from this postoperative complication. Therefore, it may be appreciated that an intraoperative assessment of tissue viability and microcirculation may be highly useful to reduce the incidence of anastomotic leakage and its comorbidities.

Frequently, intestinal microcirculation and tissue viability are assessed visually—from the color of the serosal surface, presence of bowel peristalsis, pulsation, and bleeding from the marginal arteries. While there may be high confidence that visual assessment alone may properly categorize tissue perfusion as being normal or obviously impaired, some tissues may be difficult to visually categorize. A visual approach can be highly subjective and dependent on the experience level of the surgeon. It may also be deceptive. Tissues having a dark hue may have transient venous insufficiency, while the bowel may in fact be viable. Conversely, an arterial occlusion may appear normal in its early stages. In some clinical studies, visual assessment of bowel viability was only 60% accurate.

Given the uncertainty of accurate visual determination of tissue viability, a surgeon may remove a greater amount of intestine than required for tumor resection to assure healthy tissue at the anastomosis. This approach may lead to excessive intestinal resection that may result in intestinal failure. Even an inch of preserved intestinal tissue can determine a difference between a patient being able to absorb adequate oral diet or rely on permanent parenteral nutrition, a costly consequence of colorectal surgery. Therefore, a more objective, accurate, and easy-to-perform intraoperative technique to assess tissue viability may be needed.

SUMMARY

In an embodiment, a method of assessing tissue viability may include providing at least one source of thermal stimulation of a tissue, in which the source of thermal stimulation provides at least one thermal stimulus, providing a measurement system for obtaining response data related to at least one response by the tissue to at least one thermal stimulus, applying the thermal stimulus to the tissue, measuring, using the measurement system, at least some tissue response data related to a response of the tissue to the thermal stimulus, calculating, by an electronic system, a comparison between the tissue response data and at least one viability threshold value, and determining, by the electronic system, the tissue viability based at least in part on the comparison.

In an embodiment, a system for assessing tissue viability may include at least one source of a thermal stimulus for a tissue; and a measurement system configured to receive at least some response data from the tissue.

BRIEF DESCRIPTION OF THE DRAWINGS

FIGS. 3A-C illustrate examples of a variety of possible tissue responses to a variety of thermal stimuli in accordance with the present disclosure.

FIG. 5 illustrates an embodiment of an electronic system that may be part of a system for non-contact thermography for determining tissue viability in accordance with the present disclosure.

DETAILED DESCRIPTION

As disclosed above, determination of tissue viability during and after surgery may be an important predictor of surgical success. Tissue viability may be determined in a number or ways, including an assessment of tissue color, tissue activity such as contractility, and bleeding at anastomotic edges. A factor in tissue viability may also include proper microperfusion of the tissue. Tissue color may be one method of assessing degrees of microperfusion. Another method of determining microperfusion may be through a measurement of heat transfer through the tissue.

Blood flow through a tissue may provide oxygen, nutrients, and a means of removing metabolic toxins. In addition, blood flow may assist in maintaining thermal regulation of tissue. Therefore, it may be appreciated that the ability of a portion of tissue to maintain its temperature at normal physiological values may be an indication of blood flow through the tissue, and thus may be one measure of its potential viability.

Figure 1A:
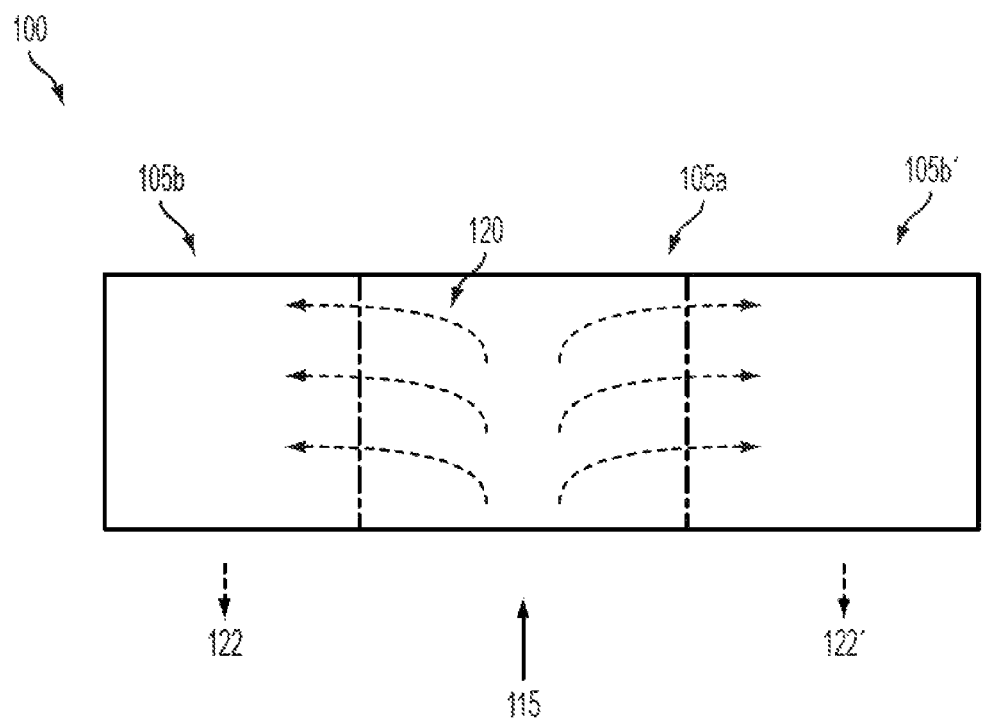
FIG. 1A illustrates an example of tissue thermal conduction without blood perfusion in accordance with the present disclosure.
Figure 1B:
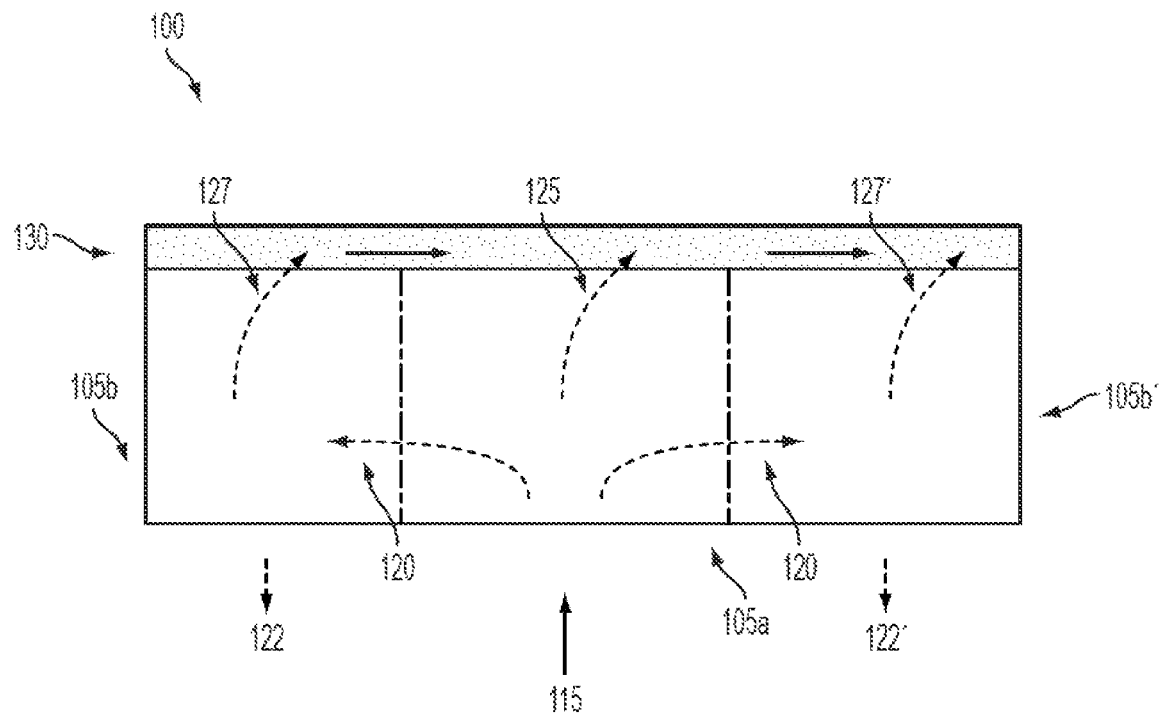
FIG. 1B illustrates an example of tissue thermal conduction with blood perfusion in accordance with the present disclosure.

Dynamic thermography may be one method to determine the ability of a portion of tissue to main physiological temperatures by measuring its response to one or more thermal stimuli. Healthy and impaired tissue may exhibit different patterns of response to a thermal stimulus. Impaired microcirculation may diminish heat dissipation within tissue. Thus, poorly perfused tissue may not return to physiological temperatures after receiving a thermal stimulus in the same manner as well perfused tissues. FIGS. 1A and 1B illustrate some differences in thermal response of poorly perfused versus well perfused tissues.

FIG. 1A illustrates a section of tissue 100 composed of a portion 105a receiving a thermal stimulus 115, and its neighboring portions of tissue 105b,b' that do not receive the thermal stimulus. It may be understood that a thermal stimulus 115 may include either heat (deposition of energy into the tissue) or cold (removal of energy from the tissue). A significant mechanism of heat transfer in solid or semi-solid material, such as tissue, may include thermal diffusion. Parameters related to thermal diffusion may include a thermal diffusivity ($\alpha$), a thermal conductivity ($\lambda$), and a specific heat capacity (Cp). These thermal diffusion parameters may be dependent on at least some properties of the specific material. Thus, for muscle tissue, $\lambda$, may be about 0.38 to about 0.54 W/mK, Cp may be about 3.6 to about 3.8 kJ/kgK, and $\alpha$ may be about $0.9 \times 10^{-7}$ to about $1.5 \times 10^{-7}$ m$^2$/sec. In contrast, for fat tissue, $\lambda$, may be about 0.19 to about 0.2 W/mK, Cp may be about 2.2 to about 2.4 kJ/kgK, and $\alpha$ may be about $0.96 \times 10^{-7}$ m$^2$/sec.

FIG. 1A illustrates an example of thermal energy transfer into, within, and from a piece of tissue 100. In FIG. 1A, thermal energy such as thermal stimulus 115 may be applied to a portion of tissue 105a and may thereafter be transferred via thermal diffusion 120 into neighboring tissue portions 105b,b'. If the neighboring tissues 105b,b' have the same general tissue make-up as the portion of tissue 105a, then the thermal transfer 120 into the neighboring tissues may have about the same thermal diffusivity as the tissue under stimulus. Hence, the neighboring portions of tissue 105b,b' may have essentially the same dynamic thermal response to the stimulus 115 as would the portion of tissue 105a under stimulus.

In addition to the thermal energy transfer 120 between neighboring portions of tissue 105b,b', thermal energy may also be transferred away from the tissue 100 to the environment 122,122' by several mechanisms including radiant transfer and convective transfer. However, radiant and convective transfer may not be as efficient as thermal diffusion for transferring thermal energy.

FIG. 1B illustrates an example of thermal energy transfer into, within, and from a piece of tissue 100 that is perfused with a blood supply 130. For the purpose of example only, the thermal diffusion parameters of blood may be taken as being essentially the same as muscle tissue (for blood, $\lambda$, may be about 0.49 W/mK, Cp may be about 3.6 kJ/kgK, and $\alpha$ may be about $1.3 \times 10^{-7}$ m$^2$/s). Therefore, the diffusion of thermal energy into blood from tissue 105a under thermal stimulus 115 may have substantially the same dynamic profile as thermal diffusion 120 into neighboring tissues 105b,b'. However, if blood perfusion is sufficient (arrows within blood supply 130), blood with excess or reduced temperature due to thermal transfer from tissue 105a may be constantly replaced by blood at normal physiological temperature. Thus the blood flow 130 may represent a constant thermal sink (or source). It may be appreciated that the blood flow 130 effecting thermal transfer 125 from or into tissue 105a may have the same effect on neighboring tissues 105b,b' as indicated by 127 and 127'.

Thus, it may be appreciated that a dynamic temperature profile of tissue 105a undergoing thermal stimulus 115 may reflect the tissue environment. Specifically, the dynamic temperature profile may depend on whether thermal transfer 120 only occurs with other neighboring solid tissue 105b,b', or whether thermal transfer also includes transfer 125, 127, 127' to a flowing blood supply 130 of effectively constant temperature.

A thermal stimulus may represent exposing some portion of tissue to either a heated or a cooled environment. It may be understood that one or more thermal stimuli may be applied to a tissue portion or to multiple tissue portions. If multiple tissue portions receive thermal stimuli, the portions may be contiguous, non-contiguous, or include both contiguous and non-contiguous portions. If multiple tissue portions receive thermal stimuli, all of the tissue portions may receive effectively the same stimuli. Alternatively, a tissue portion may receive one or more thermal stimuli that differ from the one or more thermal stimuli received by another tissue portion.

Prior to the application of a thermal stimulus, tissue under assessment may have a baseline temperature at effectively normal core body temperature. Normal core body temperature for adult humans may be about 35.5° C. (95.9° F.) to about 37.5° C. (99.5° F.), although this value may vary depending on the health and environment of the tissue being measured. While tissue viability may be measured by the tissue response to thermal stimuli, it may be appreciated that the thermal stimuli should not cause the tissue to attain a temperature outside a safe range, which may be defined by a safe maximum tissue temperature at the higher end of the range, and a safe minimum tissue temperature at the lower end of the range. A safe maximum tissue temperature may be about 37° C. (about 98.6° F.) to about 42° C. (about 107.6° F.). Examples of a safe maximum tissue temperature may include, without limitation, about 37° C. (about 98.6° F.), about 38° C. (about 100.4° F.), about 39° C. (about 102.2° F.), about 40° C. (about 104° F.), about 41° C. (about 105.8° F.), about 42° C. (about 107.6° F.), and ranges between any two of these values. A safe minimum tissue temperature may be about 32° C. (about 89.6° F.) to about 37° C. (about 98.6° F.). Examples of a safe minimum tissue temperature may include, without limitation, about 32° C. (about 89.6° F.), about 33° C. (about 91.4° F.), about 34° C. (about 93.2° F.), about 35° C. (about 95° F.), about 36° C. (about 96.8° F.), about 37° C. (about 98.6° F.), and ranges between any two of these values.

A safe maximum stimulus temperature may be defined as a stimulus temperature that, when applied to a tissue for a period of time, may heat the tissue to a temperature that is about, but not more than, the safe maximum tissue temperature. Similarly, a safe minimum stimulus temperature may be defined as a stimulus temperature that, when applied to a tissue for a period of time, may cool the tissue to a temperature that is about, but not less than, the safe minimum tissue temperature.

FIGS. 2A-H illustrate non-limiting examples of possible types of thermal stimuli.

Figure 2A:
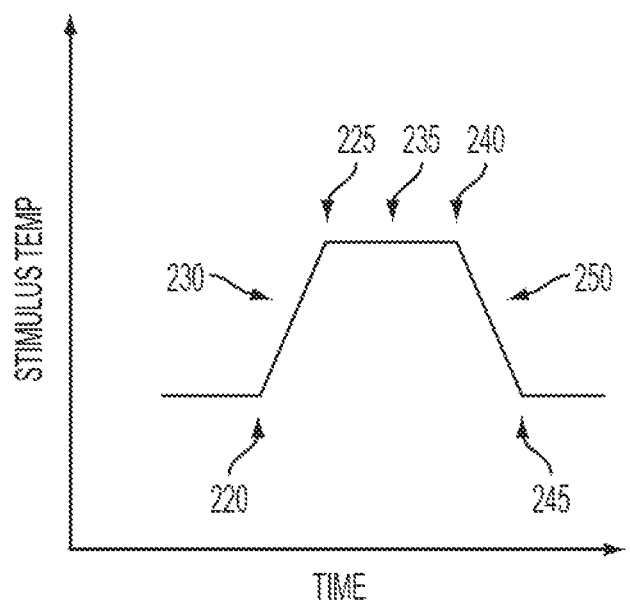
FIGS. 2A-H illustrate examples of a variety of thermal stimuli that may be applied to a tissue in accordance with the present disclosure.

FIG. 2A depicts one non-limiting example of a thermal stimulus composed of rapidly applied heat stimulus. A heat stimulus may be initiated at a heating start rise time 220 and attain a safe maximum stimulus temperature at a heating end rise time 225. A heating rise time 230 may be calculated as the difference between the heating end rise time 225 and the heating start rise time 220. It may be understood that, while the source of a heating stimulus may be effectively activated in an off-to-on transition, the actual heating stimulus may take some time to reach a maximum stimulus value at the tissue. Hence, a heating rise time 230 may have a short finite duration. The heat stimulus may be held at a safe maximum stimulus temperature for a heat stimulus hold time 235 of about 0.5 minutes to about 5 minutes. Examples of a heat stimulus hold time may be, without limitation, about 0.5 minutes, about 1 minute, about 1.5 minutes, about 2 minutes, about 2.5 minutes, about 3 minutes, about 4 minutes, about 5 minutes, and ranges between any two of these values. During the application of the heat stimulus, the tissue temperature may rise to a safe maximum tissue temperature. The end of the heat stimulus hold time 230 may correspond to a heating start fall time 240. A heating start fall time 240 may be initiated by the removal of the heating stimulus (such as turning off a heating element). The heating start fall time 240 may also be accompanied by the application of a null stimulus. A null stimulus may include the application of a temperature stimulus at either about ambient temperature or at about normal human core temperature. A heating end fall time 245 may correspond to the time at which the stimulus at the tissue either attains about ambient temperature or about normal core physiological temperature. A heating fall time 250 may be calculated as the difference between the heating end fall time 245 and the heating start fall time 240. It may be understood that, while the source of a heating stimulus may be effectively removed in an on-to-off transition, the actual heating stimulus may take some time to reach a baseline temperature value, such as around ambient temperature, at the tissue. Hence, in one non-limiting embodiment depicted in FIG. 2A, a heating fall time 250 may have a short but finite duration.

Figure 2B:
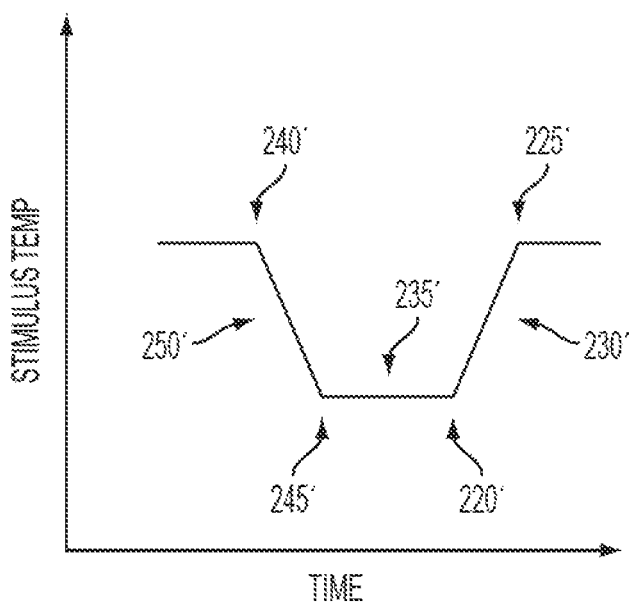

FIG. 2B depicts one non-limiting example of a thermal stimulus composed of a rapidly applied cooling stimulus. A cooling stimulus may be initiated at a cooling start fall time 240' and attain its safe minimum stimulus temperature 215 at a cooling end fall time 245'. A cooling fall time 250' may be calculated as the difference between the cooling end fall time 245' and the cooling start fall time 240'. It may be understood that, while the source of a cooling stimulus may be effectively activated in an off-to-on transition, the actual cooling stimulus may take some time to reach a minimum stimulus value at the tissue. Hence, a cooling fall time 250' may have a short finite duration. The cooling stimulus may be held at a safe minimum stimulus temperature for a cooling stimulus hold time 235' of about 0.5 minutes to about 5 minutes. Examples of a cooling stimulus hold time may be, without limitation, about 0.5 minutes, about 1 minute, about 1.5 minutes, about 2 minutes, about 2.5 minutes, about 3 minutes, about 4 minutes, about 5 minutes, and ranges between any two of these values. During the application of the cooling stimulus, the tissue temperature may fall to a safe minimum tissue temperature. The end of the cooling stimulus hold time 235' may correspond to a cooling start rise time 220'. A cooling start rise time 220' may be initiated by the removal of the cooling stimulus (such as turning off a Peltier cooler). The cooling start rise time 220' may also be accompanied by the application of a null stimulus. A null stimulus may include the application of a temperature stimulus at either about ambient temperature or at about normal human core temperature. A cooling end rise time 225' may correspond to the time at which the stimulus at the tissue either attains about ambient temperature or about normal core physiological temperature. A cooling rise time 230' may be calculated as the difference between the cooling end rise time 225' and the cooling start rise time 220'. It may be understood that, while the source of a cooling stimulus may be effectively removed in an on-to-off transition, the actual cooling stimulus may take some time to reach a baseline temperature value, such as around ambient temperature, at the tissue. Hence, in one non-limiting embodiment depicted in FIG. 2B, a cooling rise time 230' may have a short but finite duration.

It may be appreciated that a heat stimulus may be applied once or multiple times in succession. Once a tissue sample has cooled from a safe maximum tissue temperature to effectively baseline temperature at, for example, about normal human core temperature, some inter-heating time may elapse before the heat stimulus may be reapplied. A null stimulus may be applied to a tissue between two successive heat stimuli. The tissue may remain essentially at the baseline temperature during an application of a null stimulus for a null stimulus hold time of about 0 minutes to about 5 minutes. Examples of a null stimulus hold time may be, without limitation, about 0 minutes, about 0.5 minutes, about 1 minute, about 1.5 minutes, about 2 minutes, about 2.5 minutes, about 3 minutes, about 4 minutes, about 5 minutes, and ranges between any two of these values. Additionally, it may be understood that a null stimulus hold time may or may not be essentially the same between each of the multiple heat stimuli.

It may be appreciated that a cooling stimulus may also be applied once or multiple times in succession. Once a tissue sample has warmed from a safe minimum tissue temperature to effectively baseline temperature at, for example, about normal human core temperature, some period of time may elapse before the cooling stimulus may be reapplied. A null stimulus may be applied to a tissue between two successive cooling stimuli. The tissue may remain essentially at the baseline temperature during an application of a null stimulus for a null stimulus hold time of about 0 minutes to about 5 minutes. Examples of a null stimulus hold time may be, without limitation, about 0 minutes, about 0.5 minutes, about 1 minute, about 1.5 minutes, about 2 minutes, about 2.5 minutes, about 3 minutes, about 4 minutes, about 5 minutes, and ranges between any two of these values. Additionally, it may be understood that a null stimulus hold time may or may not be essentially the same between each of the multiple cooling stimuli.

It may be appreciated that the duration of any heating, cooling, or null stimulus may lead to an application of a series of thermal stimuli that may last less than 5 minutes total. In some non-limiting examples, a total duration of a series of thermal stimuli may be about 30 seconds to about 5 minutes. Non-limiting examples of the total duration of an applied thermal stimulus may include about 0.5 minutes, about 1 minute, about 1.5 minutes, about 2 minutes, about 2.5 minutes, about 3 minutes, about 3.5 minutes, about 4 minutes, about 4.5 minutes, about 5 minutes, and ranges between any two of these values. As a result of short stimulus durations, there may be a minimal impact on surgery time. A short duration of a thermal stimulus test may also permit a viability measurement to be repeated intra-operatively to confirm previous measurements thereby increasing confidence in the measurements and its conclusions.

It may also be appreciated that a heat stimulus may include one or more intermediate heating hold points during its application. Thus, the tissue may be heated to some intermediate warm temperature that is lower than the safe maximum tissue temperature. The tissue may be held at an intermediate warm temperature for an intermediate heating hold time. Thereafter, the tissue may be heated further until the tissue attains a safe maximum tissue temperature. Similarly, once the tissue has attained a safe maximum tissue temperature, the tissue may be cooled or allowed to cool to an intermediate warm temperature and held at that intermediate warm temperature for a period of time before being cooled or allowed to cool back to essentially the baseline temperature. It may be appreciated that any number of intermediate warming or cooling steps may occur over the course of a heating stimulus. Any one or more of these intermediate temperatures may be held for any appropriate period of time. It may further be appreciated that the hold times of the intermediate warming and/or cooling steps may effectively be the same or may differ.

It may also be appreciated that a cooling stimulus may include one or more intermediate cooling hold points during its application. Thus, the tissue may be cooled to some intermediate cool temperature that is greater than the safe minimum tissue temperature. The tissue may be held at an intermediate cool temperature for an intermediate cooling hold time. Thereafter, the tissue may be cooled further until the tissue attains a safe minimum tissue temperature. Similarly, once the tissue has attained a safe minimum tissue temperature, the tissue may be heated or allowed to warm to an intermediate cool temperature and held at that intermediate cool temperature for a period of time before being heated or allowed to warm back to essentially the baseline temperature. It may be appreciated that any number of intermediate warming or cooling steps may occur over the course of a cooling stimulus. Any one or more of these intermediate temperatures may be held for any appropriate period of time. It may further be appreciated that the hold times of the intermediate warming and/or cooling steps may effectively be the same or may differ.

Figure 2C:
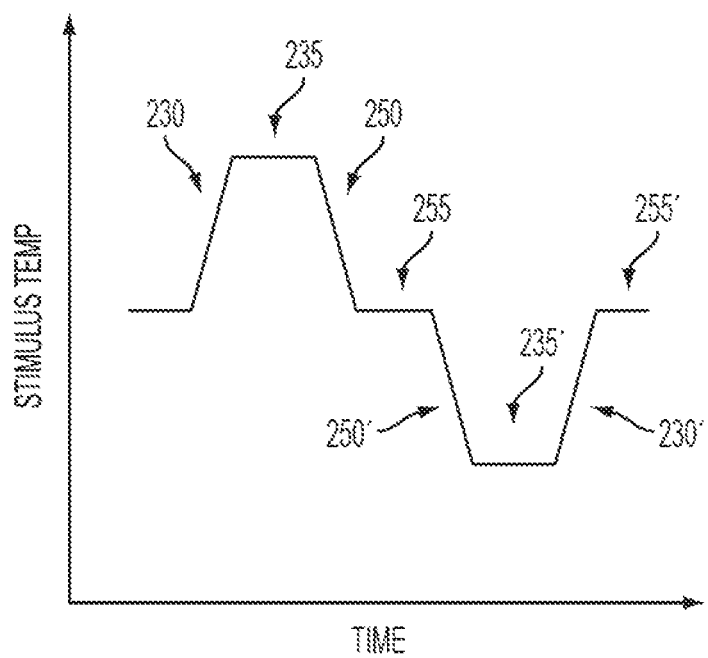
Figure 2D:
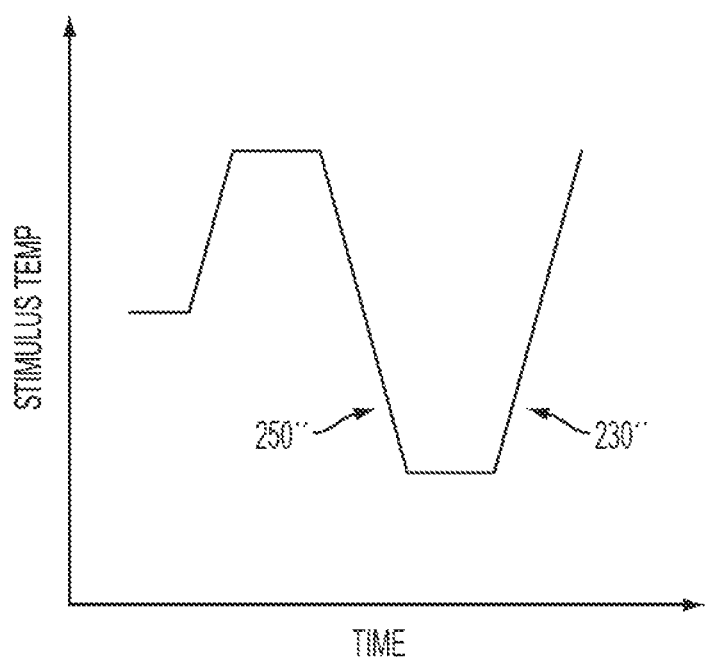

In another non-limiting embodiment of a thermal stimulus, tissue may be exposed to alternating heat stimuli and cold stimuli. FIGS. 2C and 2D illustrate two of such embodiments. FIG. 2C illustrates an embodiment in which a tissue may be exposed first to a heat stimulus having a heating rise time 230, a heating temperature hold time 235, and a heating fall time 250. The tissue may then remain at effectively the baseline temperature for a null stimulus hold time 255. Thereafter, the tissue may then be exposed to a cooling stimulus having a cooling fall time 250', a cooling temperature hold time 235', and a cooling rise time 230'. The tissue may then remain at effectively the baseline temperature for a null stimulus hold time 255' until a subsequent heat stimulus.

It may be understood that a safe maximum stimulus temperature hold time 235 and safe minimum stimulus temperature hold time 235' may be essentially the same or may differ throughout a sequence of thermal stimuli. Similarly, a heating rise time 230 may be essentially the same as, or may differ from a cooling rise time 230', and a heating fall time 250 may be essentially the same as or may differ from a cooling fall time 250'. Further, it may be understood that parameters characterizing each thermal stimulus as part of a sequence of thermal stimuli—rise time, hold time, fall time, time for the application of null stimuli—may be the same for or may differ between the stimuli.

In another non-limiting embodiment of a group of thermal stimuli, FIG. 2D illustrates a succession of applied heat stimuli and cold stimuli. FIG. 2D differs from FIG. 2C in that effectively no null stimulus times (255, 255') may be present. It may be observed, therefore, that a tissue may be subject first to a heat stimulus and then a cold stimulus with no intervening time between. Consequently, a fall time 250" may constitute the removal of a heat stimulus followed effectively immediately by the application of a cold stimulus. Similarly, a rise time 230" may constitute the removal of a cold stimulus followed effectively immediately by the application of a heat stimulus.

Figure 2E:
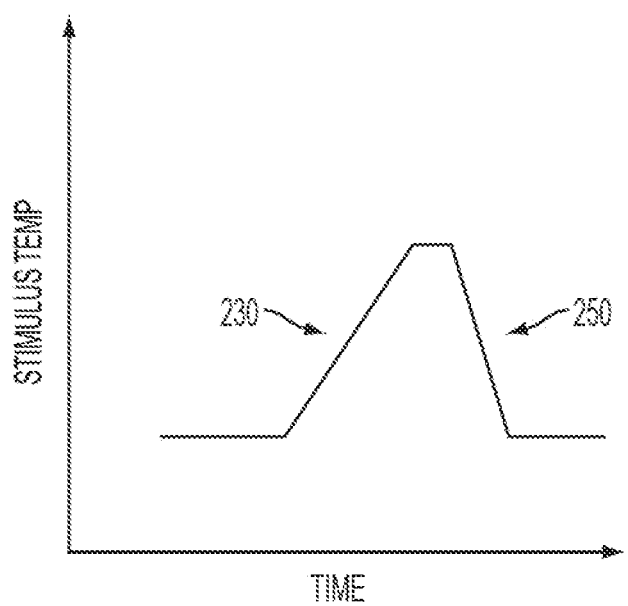
Figure 2F:
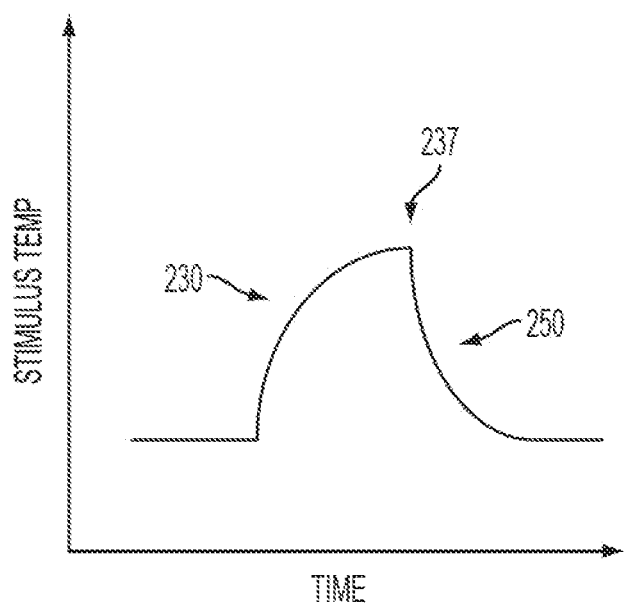

FIGS. 2E and 2F illustrate additional non-limiting embodiments of thermal stimuli that may be applied to a tissue. It may be noted that in FIGS. 2A-D, the thermal stimuli may be applied quickly resulting in short rise times (230, 230', 230") or fall times (250, 250', 250"). FIG. 2E illustrates a rise time, such as 230 and fall time, such as 250, that may take on the form of longer and more controlled linear ramps as opposed to sudden changes in stimulus application. FIG. 2E illustrates an example in which a rise time 230 and a fall time 250 may have different absolute values in their respective slopes. FIG. 2F illustrates a rise time, such as 230, and a fall time, such as 250, that may have non-linear shapes, such as exponential rises and falls. It may be appreciated further that a complex stimulus profile, that may include a variety of linear and non-linear rise and fall times, may result in the tissue not being held for any appreciable time at either a safe maximal tissue temperature or a safe minimal tissue temperature. Rather, there may be an effective time point 237 at which time a first thermal stimulus may be replaced by a second thermal stimulus of an opposite type. Although FIGS. 2E and 2F depict heating stimuli only, it may be appreciated that similar stimulus waveforms may be presented in cooling stimuli as well.

Figure 2G:
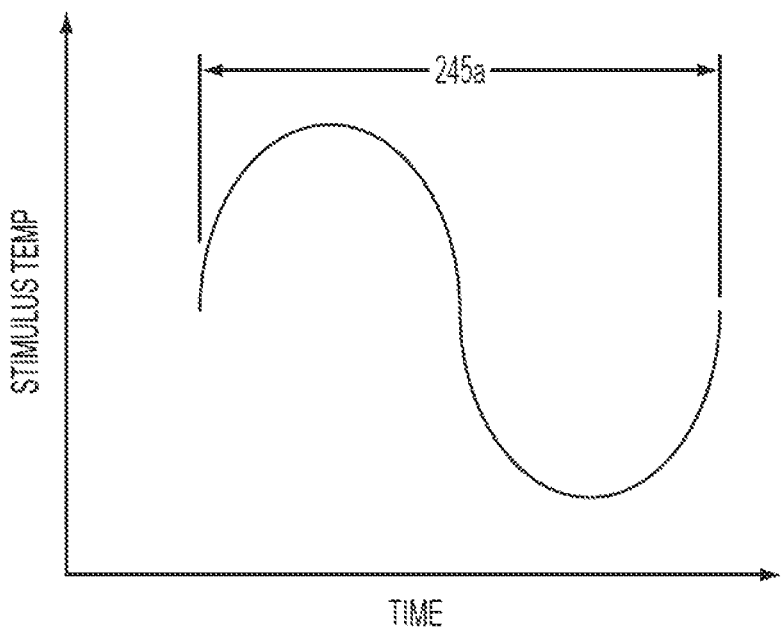
Figure 2H:
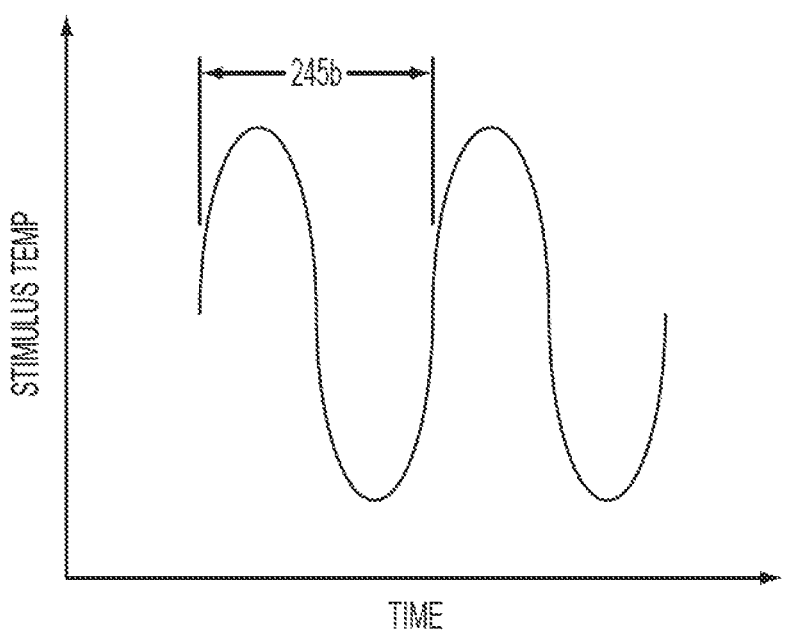

FIGS. 2G and 2H illustrate still other embodiments of thermal stimuli that may be applied to a tissue. Both FIGS. 2G and 2H illustrate an application of an essentially sinusoidal thermal stimulus with a safe maximum stimulus temperature 210 and a safe minimum stimulus temperature 215. In addition to the maximum and minimum temperatures attained by the tissue, such sinusoidal stimuli may also be characterized by a repeating period 245a,b. A long repeating period 245a may correspond to a low stimulus frequency, while a short repeating period 245b may correspond to a high stimulus frequency.

It may be observed that FIGS. 2C, 2D, 2G, and 2H depict alternating heat stimulus and cooling stimulus cycles that begin with a heat stimulus. It may be appreciated that other series of thermal stimuli may be provided. In one non-limiting example, a series of thermal stimuli may alternate between a cooling stimulus and a heat stimulus, starting with a cooling stimulus. In another non-limiting example, a series of thermal stimuli may include repeated heat stimuli. In still another non-limiting example, a series of thermal stimuli may include repeated cooling stimuli. It may be appreciated that any series of heat and/or cooling stimuli may be applied in a series.

As disclosed above, tissue viability may depend at least in part on the degree of microvascular perfusion of the tissue. Microvascular perfusion may be assessed in terms of the ability of a tissue to maintain its temperature during exposure to imposed thermal stimuli or to recover from exposure to such stimuli. The thermal response of a tissue may be obtained by measuring and recording the tissue temperature before, during, and after one or more thermal stimuli.

Figure 3A:
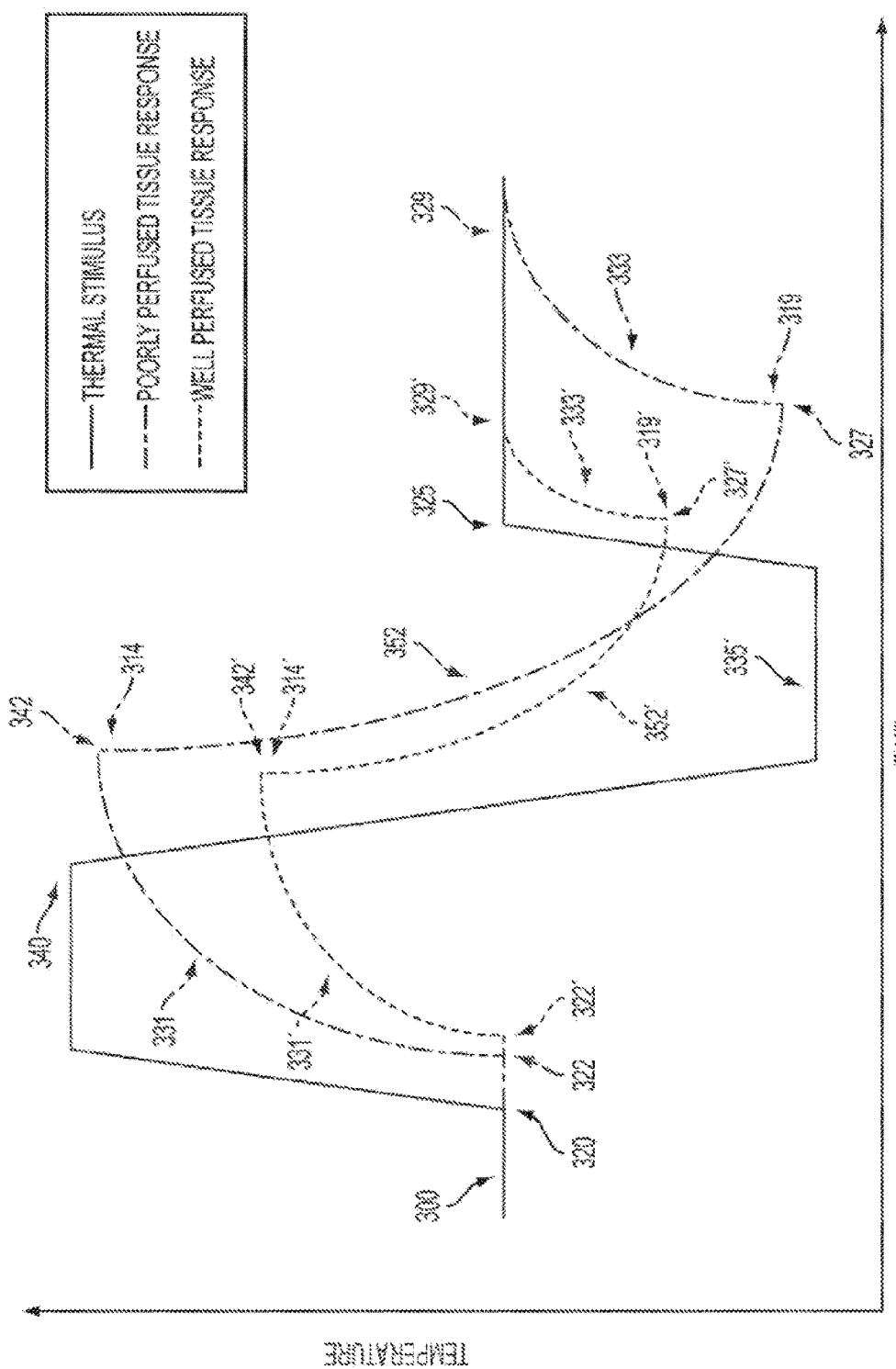

One non-limiting assessment of tissue viability may be to measure, record, and analyze a response of a tissue to a sudden change in temperature. It may be understood that a "sudden" change in temperature may include a limiting but non-zero rise or fall time in the stimulus temperature as the thermal stimulus may be rapidly applied or removed. It may be appreciated that even if a thermal stimulus may be rapidly activated (for example, a heating coil may be turned on), the resulting thermal stimulus arriving at the tissue under test may take some finite time to reflect such an application and stabilize at a final temperature. The response to such a "sudden" change in stimulus temperature may be characterized as an impulse response. A tissue impulse response may be characterized by one or more tissue impulse response metrics. FIG. 3A illustrates embodiments of possible responses of poorly perfused tissue and well perfused tissue to a thermal stimulus 300 corresponding to a rapid application of a sudden heat stimulus followed essentially immediately by a sudden cold stimulus. At a heating stimulus time point 320, a heat stimulus may be applied to a tissue. At a cooling stimulus time point 340, a cold stimulus may be applied to a tissue. At an end stimulus time point 325', either no thermal stimulus may be applied, or a null thermal stimulus may be applied.

An impulse response of a tissue to one or more thermal stimuli may be characterized by a number of metrics. The metrics may be used to assess the degree of perfusion of a tissue and thus its viability. One non-limiting metric may be an onset time of a tissue response (322, 322') to an initial heating stimulus. A poorly perfused tissue may begin its response onset time 322 shortly after being exposed to the heat stimulus. A well perfused tissue, however, may have a longer response onset time 322' because the microperfusion may buffer the build-up of detectable heat in the tissue. Both well and poorly perfused tissues may be characterized in terms of the shape of their respective temperature rise responses (331, 331'). In one non-limiting example, the shape of a tissue response curve to a heat stimulus may be characterized by a tissue heating time constant. One example of a tissue heating time constant may be a linear slope; in another example, a tissue heating time constant may be an exponential time constant. Thermal buffering due to competent blood flow may lead to a reduced tissue heating time constant in the temperature rise of well perfused tissue 331' compared to poorly perfused tissue 331. The difference in temperature rise time characteristics between the two tissues may result in a difference in tissue maximum attained temperature (314, 314'). FIG. 3A illustrates that a poorly perfused tissue may tend to achieve a higher maximum attained temperature 314 than a well perfused tissue 314'.

At the end of a heat stimulus 340, a cold stimulus may be applied to a tissue. In one non-limiting example of a response, a poorly perfused tissue may begin a fall time 342 of its temperature near the time that the heat stimulus is removed 340, and a well perfused tissue may begin its fall time 342' later than the fall time 342 of the poorly perfused tissue. In another non-limiting example of a response, poorly perfused tissue may begin a temperature fall time 342 after a well perfused tissue may begin its temperature fall time 342'. A delay in the fall time 342 of poorly perfused tissue may result from a thermal capacity of the tissue receiving the thermal stimulus along with its neighboring tissue. Well-perfused tissue may initiate a temperature fall time 342' earlier than the poorly perfused tissue because both the external stimulus and the thermal regulation of the blood flow may work in concert to lower the temperature of the well-perfused tissue.

As illustrated in FIG. 3A, a tissue may be subjected to a cold stimulus immediately after being subjected to a heat stimulus. The shape of the tissue response to the subsequent application of a cold stimulus, 352, 352', may also be a useful metric to distinguish poorly perfused tissue from well-perfused tissue. In one non-limiting example, the shape of a tissue response curve to a cold stimulus may be characterized by a tissue cooling time constant. One example of a tissue cooling time constant may be a linear slope; in another example, a tissue cooling time constant may be an exponential time constant. Poorly perfused tissue may demonstrate a cooling response curve 352 having an essentially similar, if inverted, shape compared to its heating response curve 331. The response of well-perfused tissue 352' may be more complex. In one non-limiting example, a well-perfused tissue may demonstrate a cooling response curve 352' that may be characterized by a tissue cooling time constant less than that of poorly perfused tissue 352 while the tissue is above normal physiological temperatures. This effect may reflect that both the stimulus and blood flow may act together to reduce tissue temperature to its normal physiological temperature. However, once the well-perfused tissue attains a temperature below physiological normal values, the thermal effect of the blood flow may counter the additional cooling of the external stimulus. As a result, a tissue cooling time constant associated with the cooling response of well-perfused tissue 352' during this phase of a cooling stimulus may be less than that of poorly perfused tissue 352. As a result of these thermal processes, a final cold temperature attained by poorly perfused tissue 319 may be lower than, essentially the same as, or even greater than, the final cold temperature attained by the well-perfused tissue 319'.

Once the cold stimulus has been removed or a null stimulus—such as a stimulus at about normal physiological or ambient temperature—has been applied 325, both poorly perfused and well-perfused tissues may return to effectively normal physiological temperatures. Metrics that may be used to differentiate poorly perfused tissue from well-perfused tissue during this phase of the stimulus may include, without limitation, a time at which the tissue begins to recover to normal temperature (327, 327'), a characterization of the recovery curve (333, 333') such as by a thermal recovery time constant, and an approximate time at which the tissue attains essentially normal physiological temperature (329, 329'). Since well-perfused tissue may have a blood flow acting to restore the tissue to normal physiological temperatures, removal of a cold stimulus, or addition of a null stimulus may act in concert with the blood flow to restore the tissue to normal temperatures. As a result, the well perfused tissue may begin its recovery 327' sooner than poorly perfused tissue 327. A recovery curve of well-perfused tissue 333' may be characterized by a recovery time constant that is smaller than an equivalent recovery time constant that may be associated with a recovery curve of poorly perfused tissue 333. In addition, the well-perfused tissue may attain essentially normal temperatures at a time 329' earlier than that which may be attained by a poorly perfused tissue 329.

It may be appreciated that a particular tissue undergoing thermal stimuli as depicted in FIG. 3A may be characterizable by some or all of the non-limiting examples of response metrics as disclosed above. For example, a tissue displaying complex responses to thermal stimuli may be characterizable by multiple tissue heating, cooling, and/or recovery time constants. Further, depending on the specific response of a tissue, other metrics not explicitly disclosed above may be found useful to characterize a difference between well and poorly diffused tissue. Such additional or alternative tissue response metrics may be considered within the scope of this disclosure.

Figure 3B:
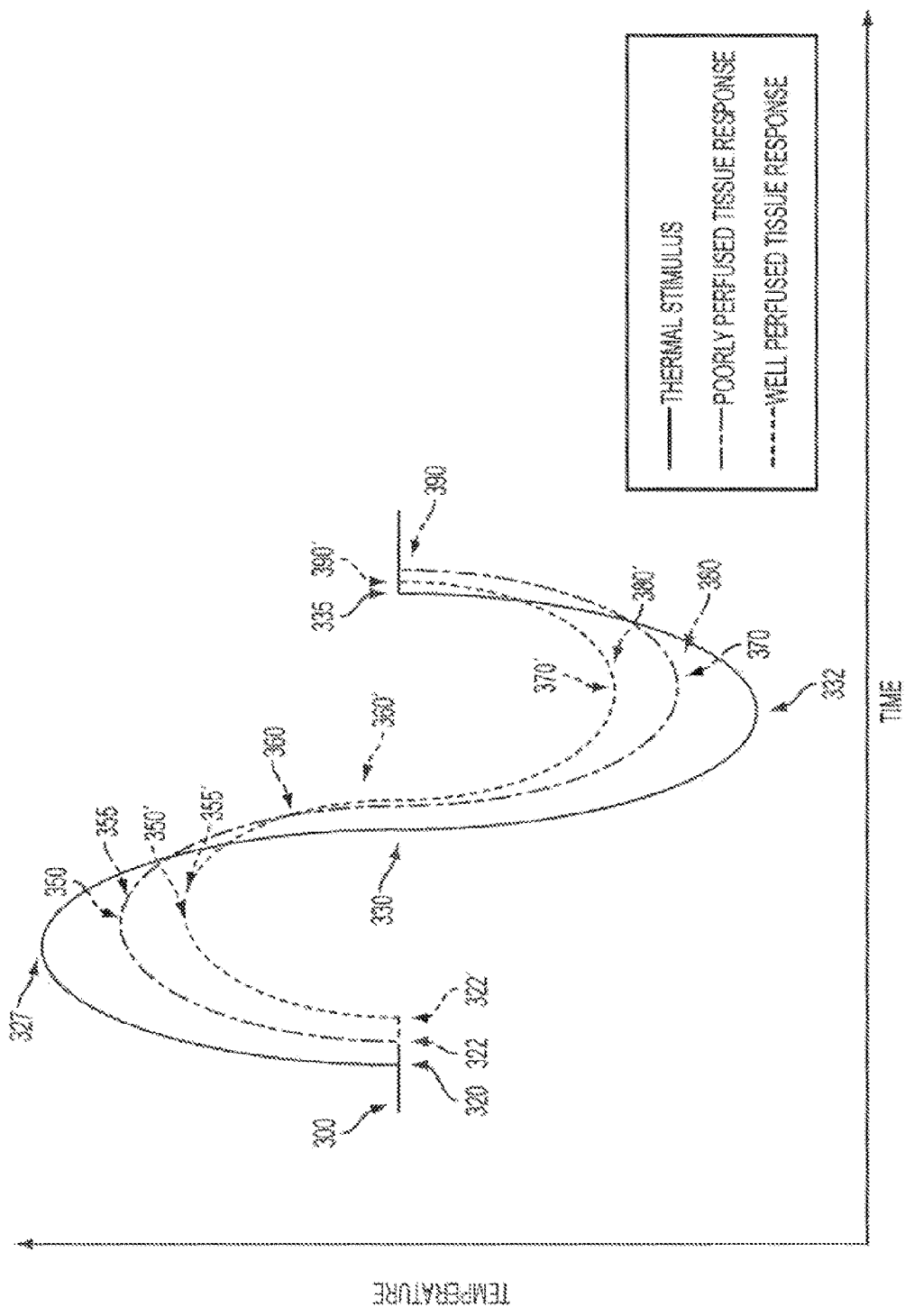

An alternative method of characterizing tissue may be to expose a tissue to a time varying stimulus that may continuously range between a safe maximum stimulus temperature and a safe minimum stimulus temperature. FIGS. 2G and 2H illustrate one type of stimulus that may be used to expose a tissue to continuously varying temperature stimuli over time. The use of such continuously varying temperature may be referred to as lock-in thermography. Alternative terminology may include frequency response thermography. FIGS. 3B and 3C illustrate possible tissue responses to such frequency response thermography.

FIG. 3B illustrates possible tissue responses to a thermal stimulus 300 that may vary continuously between a maximum value and a minimum value. The stimulus may begin at some initiating time 320 and may reach a safe maximum stimulus temperature at a maximum time 327. Thereafter, the stimulus may return back to a null stimulus point at a midpoint time 330 followed by attaining a safe minimum stimulus temperature at a minimum time 332. In one embodiment, the stimulus may repeat the continuously varying thermal stimulation cycle. In another embodiment, the thermal stimulus may end after returning essentially to a null stimulus at an end time 335. If the stimulus is repeated, the stimulus may be characterized as having a period $T_{St}$ that may be defined as the end time 335 minus the initiating time 320. The stimulus may also be characterized by a frequency $f_{St}$ equal to the reciprocal of $T_{St}$. Time period $T_{St}$ may be sufficiently slow so that a tissue receiving the stimulus, whether poorly perfused or well perfused, may respond to the stimulus. Examples of stimulus time periods $T_{St}$ may include, without limitation, times of about 20 sec., about 40 sec., about 1 minute, about 2 minutes, about 5 minutes, or ranges between any two of these values.

In some non-limiting examples of a method of non-contact thermographic mapping, tissue may be exposed to a continuously varying thermal stimulus having a pre-determined set time period $T_{St}$. In another non-limiting example of a method of non-contact thermographic mapping, tissue may be exposed to a set of continuously varying thermal stimuli, each stimulus having a pre-determined set time period $T_{St}$. In still another non-limiting example of a method of non-contact thermographic mapping, tissue may be initially exposed a thermal stimulus impulse. The resulting tissue response may indicate how quickly the tissue may respond to a continuously varying thermal stimulus having a specific time period $T_{St}$. Subsequent assessments of the patient's tissue may then use a continuously varying thermal stimulus having a patient-specific time period $T_{St}$ based at least in part on the tissue response to the thermal impulse stimulus. In this manner, a patient-specific continuously varying thermal stimulus may be applied to the tissue that may optimize the assessment of a patient's tissue perfusion.

Due to the difference in thermal regulation between the two types of tissue, as disclosed above, poorly perfused tissue may attain a greater maximum temperature 350 than the maximum temperature 350' attained by well perfused tissue. Similarly, the maximum temperature time 355 at which the poorly perfused tissue may attain its maximum temperature 350 may be earlier than a maximum temperature time 355' attained by well perfused tissue. Similarly, the minimum temperature attained by the poorly perfused tissue 370 may be lower than the minimum temperature attained by the well-perfused tissue 370', and the minimum temperature time of the well perfused tissue 380' may be later than the minimum temperature time of the poorly perfused tissue 380. For a sufficiently low $f_{St}$ the general temperature profile of a tissue response may effectively duplicate the profile of the stimulus, except in amplitude. However, as a tissue may be delayed in responding to the stimulus, there may be a time delay in the response as well. A maximum time delay may be the difference between the time of a tissue attaining its maximum temperature (355, 355') and the time at which the stimulus attains its maximum 327. For consistency in notation, $\Delta t_{St}$ may refer to the maximum time delay for poorly perfused tissue (time at 355 minus time at 327), and $\Delta t_{St}'$ may refer to the maximum time delay for well perfused tissues (time at 355' minus time at 327).

It may be appreciated that a similar time delay may be associated with the time of the tissues attaining their minimum temperatures with respect to the time the stimulus attains its minimum value. Thus, the minimum time delay $\delta t_{St}$ may refer to the minimum time delay for poorly perfused tissue (time at 380 minus time at 332), and $\delta t_{St}'$ may refer to the minimum time delay for well perfused tissues (time at 380' minus time at 332). In some non-limiting examples of tissue responses, $\Delta t_{St}$ may be essentially the same as $\delta t_{St}$, and/or $\Delta t_{St}'$ may be essentially the same as $\delta t_{St}'$. In some other non-limiting examples of tissue responses, $\Delta t_{St}$ may differ from $\delta t_{St}$, and/or $\Delta t_{St}'$ may differ from $\delta t_{St}'$. In some non-limiting examples of tissue responses, $\Delta t_{St}$ may be essentially the same as $\Delta t_{St}'$, and/or $\delta t_{St}$ may be essentially the same as $\delta t_{St}'$. In some other non-limiting examples of tissue responses, $\Delta t_{St}$ may differ from $\Delta t_{St}'$, and/or $\delta t_{St}$ may differ from $\delta t_{St}'$.

The general shape of the tissue response of either poorly perfused or well perfused tissue may be essentially the same as the shape of the thermal stimulus, or may differ from the shape of the thermal stimulus curve. In one embodiment, the shape of the response to a thermal stimulus of poorly perfused tissue 360 may be similar to that of the shape of the stimulus. This may result from the poorly perfused tissue having no other active supply of heat (or cooling) other than the applied stimulus. Alternatively, the thermal capacitance of poorly perfused tissue may act to alter the shape of the thermal response 360 to the applied thermal stimulus. In one non-limiting embodiment, the thermal response of well perfused tissue 360' may differ from the shape of the applied thermal stimulus. This may result from the constant temperature of the perfusing blood flow. Thus, during the cooling phase of the tissue, initially the blood temperature may boost the effect of the applied thermal stimulus at least until the tissue is about the temperature of the blood supply. As the tissue is cooled further by the applied stimulus, the blood temperature may tend to resist the cooling process. As a result, the shape of the response curve of the well perfused tissue 360' may differ from that of the applied stimulus. In another, alternative embodiment, the shape of the thermal response curve of the well perfused tissue 360' may be about the same as the applied stimulus.

A tissue frequency response to lock-in thermographic techniques may also be a method to differentiate between poorly perfused and well perfused tissue. FIG. 3B illustrates one embodiment of a frequency response of poorly perfused and well perfused tissue. Each tissue may have a thermal capacitance that may retard the response of the tissue to a thermal stimulus. It may be appreciated that beyond some frequency of cycling a stimulus between a heat stimulus and a cold stimulus, a tissue may fail to respond. FIG. 3C illustrates some non-limiting examples of possible responses to higher frequency thermal stimuli. It may be appreciated that the initial response of a tissue to an input of thermal stimulus may be delayed more at higher frequencies than at lower frequencies. Thus poorly perfused tissue may initiate its response 322 to a higher frequency stimulus at a time later than the initiation of response to a lower frequency stimulus. Similarly, a well perfused tissue may initiate its response 322' to a higher frequency stimulus at a time later than the initiation of response to a lower frequency stimulus. Similarly, the maximal temperature attained by poorly perfused tissue 350 and well perfused tissue 350' may be less at higher stimulus frequencies than at lower stimulus frequencies. In addition, the time delay between the time of the stimulus maximum and the tissue response maximum may be greater at higher frequencies than at lower frequencies for both the poorly perfused tissue (time at 355 minus time at 327) and well perfused tissue (time at 355' minus time at 327).

Additional affects may also be observed. Because the well perfused tissue may have an active process to maintain its baseline temperature (blood flow), the well perfused tissue may effectively cease responding to a thermal stimulus at a frequency lower than that at which the poorly perfused tissue may effectively stop responding. Additionally, as illustrated in FIG. 3C, the well perfused tissue may initially respond to a thermal stimulus (at an onset time 322', and having a maximal temperature 350' at a maximal time 355') but its response may decrease (for example at minimal time 380' having a minimum temperature 370') over time as the thermal capacitance of the constant temperature blood flow may adapt to the thermal stimulus. In one embodiment, after some period of time at a particular thermal stimulus frequency, a well perfused tissue may no longer respond to the stimulus. In other embodiments, a well perfused tissue and a poorly perfused tissue may respond to a frequency varying thermal stimulus in any of a number of alternative manners.

Figure 4A:
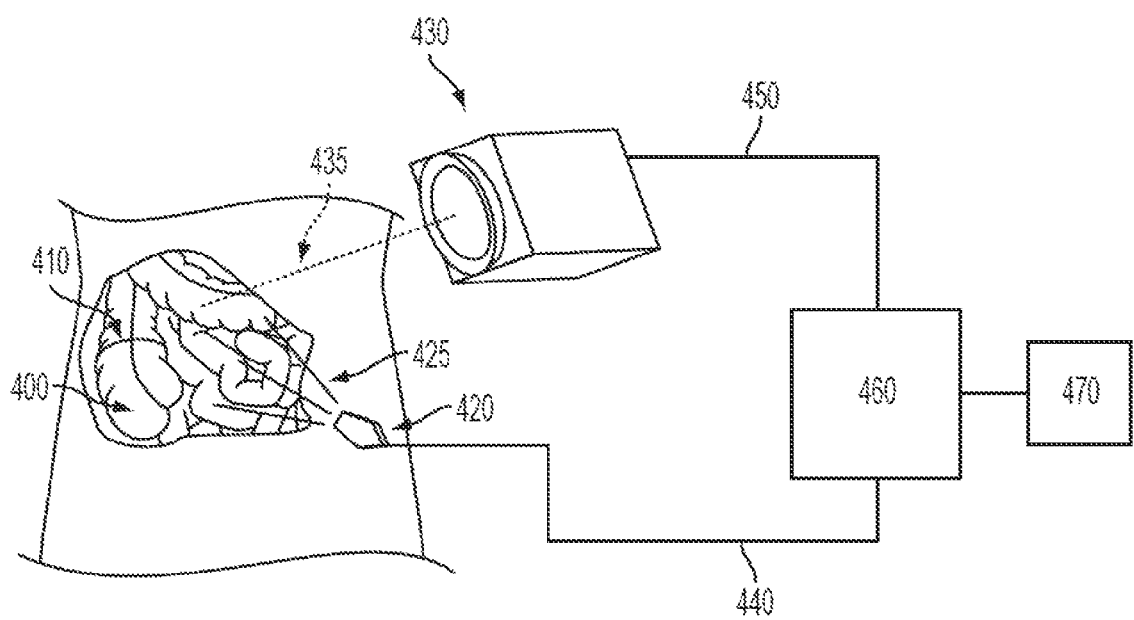
FIG. 4A illustrates an open surgical embodiment of a system for non-contact thermography for determining tissue viability in accordance with the present disclosure.
Figure 4B:
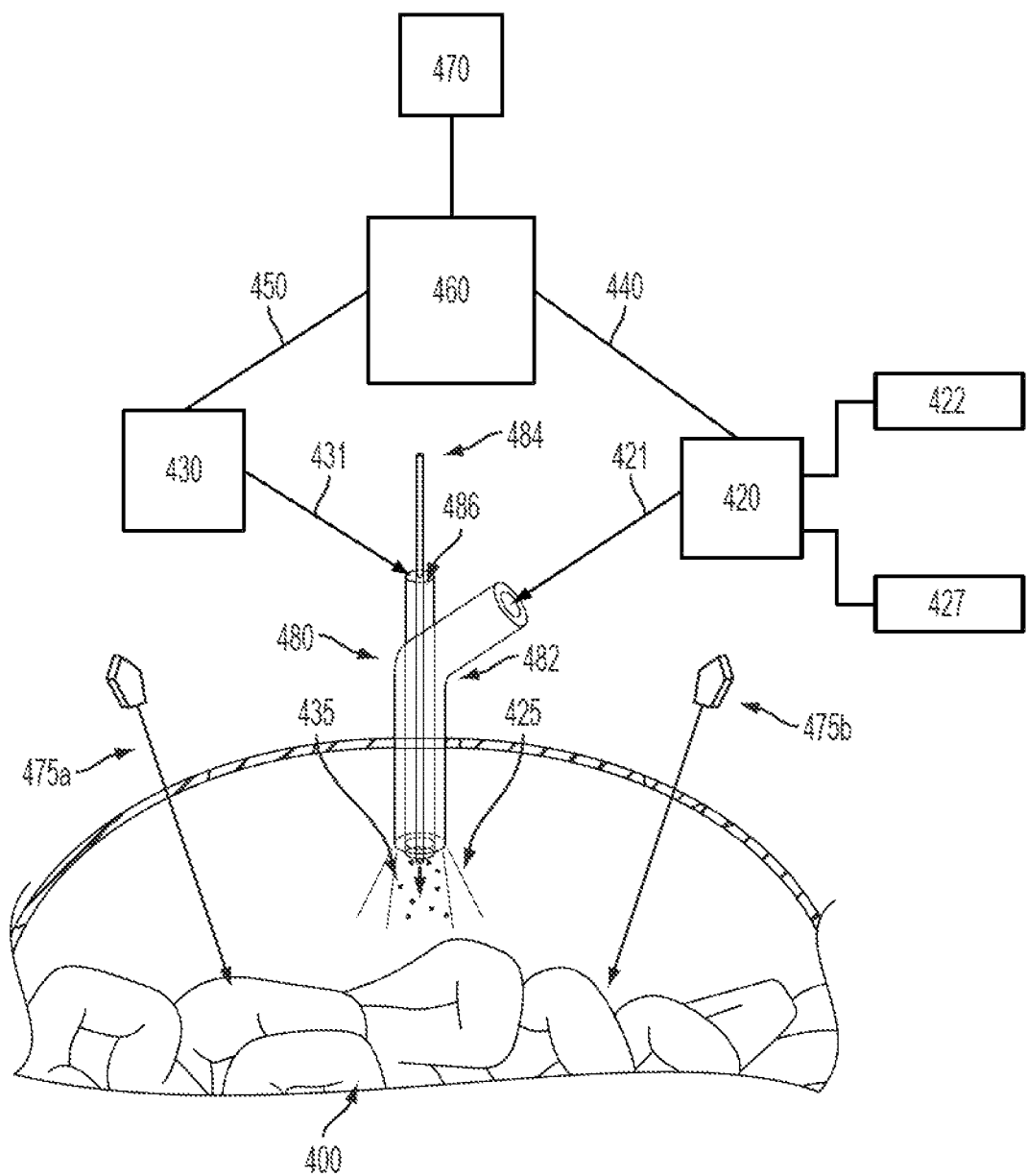
FIG. 4B illustrates a laparoscopic embodiment of a system for non-contact thermography for determining tissue viability in accordance with the present disclosure.

FIGS. 4A and 4B depict non-limiting embodiments of systems that may be used for non-contact thermal assessment of tissue viability. FIG. 4A illustrates a tissue 400 such as a resected colon. A specific area, such as an anastomosis 410, may be a portion of the tissue 400 to be assessed during and after a medical procedure. The system may be composed of a source of thermal stimulation 420, a temperature measurement system 430, and an electronic system 460 capable of controlling the source of thermal stimulation over a thermal stimulus control data line 440. The electronic system 460 may also control the measurement system 430 and/or receive tissue response data 435 from the measurement system by means of one or more measurement system control and/or data lines 450. The source of thermal stimulation 420 may provide a thermal stimulus 425 to the portion of tissue 400 for assessment. The thermal stimulus may include a heating stimulus, a cooling stimulus, or both a heating stimulus and a cooling stimulus. The temperature measurement system 430 may receive some tissue response data 435 from the tissue under assessment. Additionally, electronic system 460 may perform calculations based at least in part on the tissue response data 435 and compare the results of the calculation against one or more viability threshold values. Electronic system 460 may present any or all of the tissue response data, results of calculations, and/or results of the comparison to one or more users via an output device 470.

FIG. 4B depicts a non-limiting example of a laparoscopic embodiment of a system to use non-contact thermography to assess tissue viability. Tissue 400 may be located within an abdominal cavity. A surgical procedure may include a laparoscopic device 480 along with one or more surgical implements 475a,b. In one non-limiting embodiment, the laparoscopic device 480 may include a telescopic rod lens system. Specifically, the laparoscopic device 480 may include a means for introducing a gas 482 to insufflate the abdominal cavity, thereby creating a space in which a surgeon may deploy the surgical devices 475a,b. The gas may include any non-toxic gas including, as a non-limiting example, $CO_2$. In one embodiment, the gas source 421 for insufflation may be associated with a source of thermal stimulation 420. In one non-limiting embodiment, the insufflation gas may be cooled or heated to a desired temperature by means of a cold source 422 and a heat source 427, respectively, through a heat exchange mechanism. For example, a cold source 422 may comprise a refrigerated fluid contained in thermal exchange tubing that may be in contact with the insufflation gas. In another example, a cold source 422 may include a Peltier cooler. In one example, a heat source 427 may include a heated fluid that may be contained in a thermal exchange tubing that may contact the insufflation gas. In another example, the heat source 427 may include a hot plate or other heated surface, or a radiative heat supply such as an infrared heating lamp. A temperature of the insufflation gas may be measured at the source of the thermal stimulation by means of a temperature probe such as a thermistor, or other thermal sensing device.

It may be appreciated that use of the insufflation gas as the thermal stimulus may provide a number of benefits. The heated or cooled insufflation gas may provide thermal stimulus to large areas of the tissue so that a large area of tissue may be assessed at one time. In addition, the temperature of the insufflation gas may be rapidly changed, thereby reducing the time for assessing tissue viability. Further, the insufflation gas may not interfere with surgical tool manipulation of the tissues.

The laparoscope may also include a source of light for illuminating the surgical field, the light being directed into the abdominal cavity by such methods as a light pipe 484. The laparoscope may also include a means 486 for directing images from the surgical site to a camera or other optical sensor. Such a directing means 486 may include, without limitation, a rigid or flexible light or radiation conducting rod, or one or more fiber optic fibers disposed singly and/or in a bundle. The fiber optic cables may attach to an image magnifier that may be used by a surgeon to monitor the procedure within the abdominal cavity. Alternatively, the image direction means 486 may be associated with an optical path 431 that may be further associated with a measurement device 430. In one non-limiting embodiment, a magnification camera as used by a surgeon to visualize the surgical site may be essentially the same device as the measurement device for assessing heat response by the tissue. In another non-limiting embodiment, the means for directing images 486 may be switched from a magnifying system to an optical path 431 to direct the imaging data to a measurement device 430. In yet another non-limiting embodiment, the image directing means 486 may be split to deliver image data to both an image magnifier for the surgeon to visualize the surgical site and the measurement system 430.

It may be appreciated that a laparoscopic embodiment may also permit a thermal stimulus 425 to be applied to a tissue 400, and that thermal response data 435 may be detected by the image direction means 486 to a measurement device 430. It may further be appreciated that an electronic system 460 may be used to control the source of thermal stimulus 420 over one or more control lines 440. Electronic system 460 may also control the operation of the measurement system 430 over one or more control and/or data lines 450. Electronic system 460 may also include computing codes to analyze data from the measurement system to determine the possible viability of tissue 400 based at least in part on the data received from the measurement system 430. In one embodiment, electronic system 460 may provide at least some viability data to one or more users by means of an output device 470. In addition, the use of a laparoscopic device may permit a surgeon to perform a viability assessment after the surgery during a post-operative period.

It may be recognized that the embodiments depicted in FIGS. 4A and 4B may both be composed of at least a source of thermal stimulus 420 for a tissue 400 and a measurement system 430 configured to receive at least some thermal response data 435 from the tissue. As disclosed above, the thermal stimulus 425 may include a heating stimulus, a cooling stimulus, or a stimulus including both heating and cooling components. A heating stimulus may include, without limitation, one or more of a heated gas, infrared radiation microwave radiation, or ultrasound. Examples of heated gases may include, without limitation, air, carbon dioxide, and nitrogen. A gas may be heated directly by heating devices such as heated resistive elements. Alternatively, a gas may be heated through a gas exchange system. In addition, the gas may be filtered and/or sterile, and also may be humidified. A gas exchange system may include, as non-limiting embodiment, a cooling source 422 and a heating source 427 as depicted in FIG. 4B and as further disclosed above.

It may be appreciated that temperature-controlled humidified air may be a simple-to control method of providing both a warming and a cooling phase of a thermal challenge with a single piece of equipment. In addition, air temperature may be easily adjusted, and the thermal stimulus may be applied from a distance and may not require a direct contact with the tissue. Further, a thermal stimulus composed of a temperature controlled gas may not interfere with surgical instruments present in the operating field; it may reach both front and back portions of the bowel, and surgery may continue on other parts of the bowel during the tissue viability assessment.

In an embodiment in which a heating thermal stimulus 427 incorporates a source of infrared radiation, infrared radiation devices may include, without limitation a heat lamp, a glow bar, one or more IR emitting diodes, and an IR laser. Such infrared (IR) radiation devices may provide radiation at any appropriate wavelength, for example a wavelength of about 1 μm to about 12 μm. Examples of such wavelengths may include about 1 μm, about 2 μm, about 3 μm, about 4 μm, about 5 μm, about 6 μm, about 7 μm, about 8 μm, about 9 μm, about 10 μm, about 11 μm, about 12 μm, and ranges between any two of these values. Additionally, the source of infrared radiation may be a pulsed source of radiation, a continuous source of radiation, or a combination of pulsed and continuous sources. Further, some infrared radiation sources may be wavelength-controllable, for example by an electronic device. Changes in IR wavelength may be used to provide thermal stimuli to deeper portions of tissue by changing the IR radiation to a shorter wavelength.

A source of a cooling stimulus 422 may include a source of rapidly-evaporating fluid. Such a fluid may be one with a low boiling point and a high heat of evaporation. Non-limiting examples of such fluids may include tetrafluoroethane, a perfluorocarbon, a hydrofluoroether, a perfluorocarbon ether, and an alcohol. In an alternative embodiment, a cooling stimulus may be provided by a cooled gas, such as, without limitation, air, carbon dioxide, and nitrogen. A gas may be cooled directly by cooling devices such as a Peltier cooler. Alternatively, a gas may be cooled through a gas exchange system, as further disclosed above and as depicted in elements 420 and 422 in FIG. 4B.

A source of thermal stimulation may also include a funnel configured to apply a thermal stimulus to a small portion of tissue. The funnel may be stationary or movable, in order to direct the stimulus to different portions of the tissue. The funnel may also be made of a flexible material to permit repositioning, or may be made of a rigid material. In one embodiment, the funnel may have an outlet orifice having a fixed diameter. In another embodiment, the outlet orifice may be adjustable, thereby permitting the thermal stimulus to be restricted to a small portion of tissue, or a larger portion of tissue. The portion of tissue receiving the thermal stimulus may have an area of about 0.5 $cm^2$ to about 10 $cm^2$. Examples of tissue areas to receive the thermal stimulus may include about 0.5 $cm^2$, about 1 $cm^2$, about 1.5 $cm^2$, about 2 $cm^2$, about 3 $cm^2$, about 4 $cm^2$, about 5 $cm^2$, about 6 $cm^2$, about 7 $cm^2$, about 8 $cm^2$, about 9 $cm^2$, about 10 $cm^2$, and ranges between any two of these values.

In one embodiment, a measurement system 430 to measure a thermal response 435 of a tissue 400 may include a thermal sensitive camera, a data acquisition system, a data processing system, a data storage system, an interface between a thermal sensitive camera and a data system, a data system display, a device to provide hard copy of one or more outputs of a data system, a data system input, a data system communication interface, and at least one user interface device. In another embodiment, an electronic system 460 may include one or more of a data acquisition system, a data processing system, a data storage system, an interface between a thermal sensitive camera and a data system, a data system display, a device to provide hard copy of one or more outputs of a data system, a data system input, a data system communication interface, and at least one user interface device, while measurement system 430 may include a thermal sensitive camera in data communication 450 with the electronic system 460. Non-limiting examples of a thermal sensitive camera may include one or more of a photovoltaic camera, a photoconductive camera, and a thermal detector camera.

A thermal sensitive camera may be characterized at least in part by a spatial resolution, a field of view, a measurement speed, and a thermal resolution. In one embodiment, a thermal sensitive camera may have a spatial resolution of about 1 mm. In some embodiments, for example assessment of some gastrointestinal tissues, a thermal sensitive camera may have a spatial resolution of about 1 mm to about 5 mm. Non-limiting examples of a camera spatial resolution may include about 1 mm, about 1.5 mm, about 2 mm, about 2.5 mm, about 3 mm, about 3.5 mm, about 4 mm, about 4.5 mm, about 5 mm, or ranges between any two of these values. In some embodiments, a thermal sensitive camera may have a thermal resolution less than about 100 mK. In one embodiment, a thermal sensitive camera may have a thermal resolution less than about 80 mK. In one embodiment, a thermal sensitive camera may have a thermal resolution less than about 50 mK. In one embodiment, a thermal sensitive camera may have a thermal resolution of about 30 mK. In some embodiments, a thermal sensitive camera may have a field of view of about 3.2 cm. In other non-limiting embodiments, a thermal sensitive camera may have a field of view of about 5 cm to about 10 cm. Examples of thermal sensitive camera fields of view may be about 5 cm, about 6 cm, about 7 cm, about 8 cm, about 9 cm, about 10 cm, and ranges between any two of these values. In one non-limiting embodiment, a thermal sensitive camera may have a measurement time of about 100 ms. In alternative embodiments, a thermal sensitive camera may have a measurement time of about 10 ms to about 30 ms. Non-limiting examples of measurement times may include about 10 msec., about 15 msec., about 20 msec., about 25 msec., about 30 msec. or ranges between any two of these values.

Thermal sensitive cameras may include cooled thermal cameras and uncooled cameras. Non-limiting examples of cooled cameras may be those having photodetectors based on narrow gap semiconductors, such as indium antimonide, indium arsenide, lead sulfide, and lead selenide. Other cooled cameras may include quantum well infrared photodetectors. Some non-limiting examples of uncooled cameras may include pyroelectric materials, ferroelectric materials, and microbolometers. Some thermal sensitive cameras may include miniaturized infrared thermal cameras. In some non-limiting embodiments, a thermal sensitive camera may be sensitive to thermal radiation having a wavelength of about 700 nm to about 14000 nm Examples of wavelengths to which a thermal sensitive camera may respond include about 700 nm, about 800 nm, about 1000 nm, about 2000 nm, about 4000 nm, about 6000 nm, about 8000 nm, about 10000 nm, about 12000 nm, about 14000 nm, and ranges between any two of these values. In an alternative embodiment, a thermal sensitive camera may be a dual-band imaging camera. In one non-limiting embodiment, a dual-band imaging camera may be activated by a first radiation having at least one wavelength of about 3000 nm to about 5000 nm, and a second radiation having at least one wavelength of about 8000 nm to about 12000 nm. In another embodiment, a dual-band imaging camera may be activated by a first radiation having at least one wavelength of about 700 nm to about 3000 nm, and a second radiation having at least one wavelength of about 8000 nm to about 14000 nm.

As disclosed above, an electronic system (460 in FIGS. 4A and 4B) may be included in a system for non-contact thermography for tissue viability. FIG. 5 illustrates a variety of components of one non-limiting embodiment of such an electronic system 500. The electronic system may comprise a number of inputs and outputs along with internal computational and processing elements. The various components of the electronic system may be in mutual communication by means of a communications bus 505. The computational components may include at least one processor 510 in data communication with some components of computer memory, such as dynamic memory 515 and static memory 520. While only a single processor unit 510 is illustrated in FIG. 5, it is understood that such an electronic system may incorporate a number of processing units acting either sequentially or in parallel. Dynamic memory components 515 may include, without limitation, DRAMs and VRAMs. Static memory components 520 may include, as non-limiting examples, disk drives, thumb drives, flash drives, ROMs, PROMs, EPROMs, and CD-ROM drives. Static memory, dynamic memory, or both static and dynamic memory may be used to hold operating instructions and/or data for the electronic system for use in accomplishing the variety of its activities.

The electronic system 500 may receive a variety of inputs through one or more device input interfaces 535. Inputs may be received from the measurement device and/or components related to the source of thermal stimulus. Inputs from the measurement device may include, without limitation, data inputs related to the tissue response to one or more thermal stimuli, and sensor data related to the control of the measurement device, such as control of a lens aperture, depth of field, and/or exposure time. Inputs from the source of thermal stimulus may include, without limitation, data from sensors related to the operation of the source of thermal stimuli such as heat sensors. Data transmitted through one or more device input interfaces 535 may include, without limitation, serial digital data, parallel digital data, and analog data. Device input interface 535 may be one or more wired interfaces and/or a wireless interfaces including, without limitation, RF wireless interfaces, a LAN interface, a WAN interface, or an IR interface.

System user inputs may be provided through one or more user input interfaces 525. A user input interface 525 may receive data from one or more input devices including, but not limited to, a keyboard, a mouse, a voice recognition system, and a digital tablet interface.

The electronic system may also provide a number of data outputs by means of one or more device output interfaces 540. In one non-limiting example, the electronic system 500 may provide outputs to control a measurement device. Such controls may include without limitation, one or more of control of an exposure time, control of a wavelength range to be measured, control of a lens aperture, control of a focal point, control of a depth of field, or other controllable point of the measurement device. In another non-limiting example, the electronic system 500 may provide outputs to control a source of thermal stimulus. Examples of control of one or more sources of thermal stimulus may include control of a temperature, control of a time period during which a temperature is held, and control of the rate of temperature increase and/or decrease.

In addition, an electronic system 500 may include one or more user output interfaces 530. User output interfaces 530 may direct information to one or more devices used by a system user. Embodiments of such output devices may include visual monitors such as CRT monitors, LED monitors, and LCD monitors, video monitors, and auditory devices such as speakers, as non-limiting examples.

It is understood that the electronic system may also be in data communication with any number of other devices not specifically disclosed above, such as other electronic systems that may hold additional instructions and/or data for accomplishing the activities required for the thermography system. Connectivity to such additional devices may be accomplished by means of additional communication interfaces 545. In one embodiment, the electronic system may be in data communication with one or more additional computing devices to provide multi-processor computation capabilities. In another embodiment, the electronic system may communicate with a server that hosts one or more libraries of tissue thermal response data. Communication interface 545 may use any one or more communication protocols including, without limitation, wired protocols, wireless protocols, internet protocols, personal network protocols and/or IR communication protocols.

Figure 6:
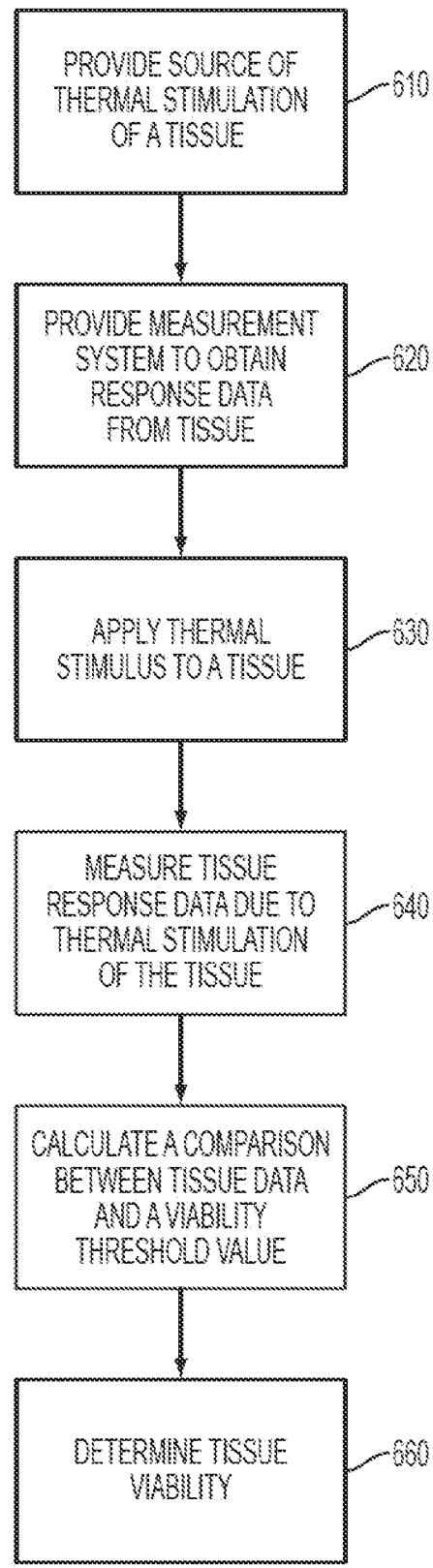
FIG. 6 is a flow chart illustrating an example of a method for assessing tissue viability by means of non-contact thermal mapping in accordance with the present disclosure.

FIG. 6 is a flow chart depicting one non-limiting embodiment of a method to assess tissue viability using non-contact thermography.

At least one source of a thermal stimulation may be provided 610 capable of providing one or more thermal stimuli. As disclosed above, such a source may be configured to provide either a heat stimulus, a cold stimulus, or both heat and cold stimuli. Alternatively, the source of thermal stimulus may provide a thermal stimulus that may vary among two or more temperatures. The stimulus may vary continuously or discretely among the temperatures.

In addition to providing 610 a source of thermal stimulation, the method may include providing 620 a measurement system for obtaining response data related to a response of the tissue to a thermal stimulus. As disclosed above, the response data may include, without limitation, data related to tissue temperature before, during, and/or after the application of one or more thermal stimuli to the tissue. The measurement system may include, as a non-limiting example, an IR sensitive camera, as disclosed above, that may measure a thermal response of the tissue. In one non-limiting example, the tissue thermal response may include a single temperature measurement of the tissue at one time point. In one non-limiting example, the tissue thermal response may include a maximum temperature of the tissue at one or more locations in the tissue at one time point. In one non-limiting example, the tissue thermal response may include the temperature of the tissue at one or more locations in the tissue over a period of time. In one non-limiting example, the tissue thermal response may include a spatial-average temperature over a portion of the tissue. In another non-limiting example, the tissue thermal response may include the temperature of the tissue at a number of discrete locations on the tissue at one or more time points. In yet another non-limiting example, the tissue thermal response may include a change in temperature over time at one or more discrete locations on the tissue. In still another non-limiting example, the tissue thermal response may include an average temperature of one or more locations of the tissue over a period of time.

The one or more thermal stimuli, as disclosed above, may then be applied 630 to a tissue in order to assess its viability. In one non-limiting embodiment, a single thermal stimulus may be applied 630 to the tissue for a period of time. In another non-limiting embodiment, a first thermal stimulus may be applied 630 to the tissue for a first period of time and then a second thermal stimulus may be applied for a second period of time. The first thermal stimulus may be a heat stimulus or a cold stimulus, and the second thermal stimulus may be a heat stimulus or a cold stimulus. The second thermal stimulus may be essentially the same as the first thermal stimulus, or it may differ. In one non-limiting example, the first stimulus may be a heat stimulus, and the second stimulus may be a cold stimulus. In another non-limiting example, the first stimulus may be a cold stimulus causing the tissue to attain one minimum tissue temperature, while the second stimulus may also be a cold stimulus that may cause the tissue to attain an essentially different minimum tissue temperature. In another non-limiting example the second thermal stimulus may be applied 630 to the tissue for a different period of time than the first thermal stimulus. In yet another non-limiting embodiment, a first thermal stimulus may be applied to the tissue for a first period, a null stimulus may be applied to the tissue for a third period of time, and then a second thermal stimulus may be applied to the tissue for a second period of time. As disclosed above, a null stimulus may be composed of a thermal stimulus at about ambient temperature, or it may be composed of a thermal stimulus at about normal physiological temperature. It may be appreciated that the first and second thermal stimuli may be essentially the same or they may differ in type (heat vs. cold), applied temperature to the tissue (heat vs warm), or duration. Additionally, the duration of the application of the null stimulus may be essentially the same as the duration of the first stimulus, or the second stimulus, or may have a duration differing from both the first and second thermal stimulus.

The one or more thermal stimuli may be composed of a heat stimulus, a cold stimulus, or a combination of heat and cold stimuli. In one non-limiting example, a heat stimulus may be one that may cause the tissue to attain a temperature of about 37° C. to about 42° C. In another non-limiting example, a heat stimulus may be one that may cause the tissue to attain a temperature of about 42° C. In yet another non-limiting example, a cold stimulus may be one that may cause the tissue to attain a temperature of about 32° C. to about 37° C. In still another non-limiting example, a cold stimulus may be one that may cause the tissue to attain a temperature of about 32° C.

The one or more thermal stimuli may be applied 630 to the tissue for any appropriate duration. In one non-limiting example, a heat stimulus may be applied 630 to the tissue for about 0.5 minutes to about 5 minutes. In another non-limiting example, a heat stimulus may be applied 630 to the tissue for about 1 minute. In yet another non-limiting example, a cold stimulus may be applied 630 to the tissue for about 0.5 minutes to about 5 minutes. In still another non-limiting example, a cold stimulus may be applied 630 to the tissue for about 1 minute. In still another non-limiting example, a null stimulus may be applied 630 to the tissue for about 0 minutes to about 5 minutes. In still another non-limiting example, a null stimulus may be applied 630 to the tissue for about 0 minutes.

The thermal response of the tissue may be measured 640 before, during, and/or after the application of the one or more thermal stimuli. As disclosed above, the measurement may include the measurement of tissue temperature by a measuring system that may include a thermal sensitive camera. Such a thermal sensitive camera may be a camera sensitive to thermal radiation emitted by the tissue. Measurement protocols may include lock-in thermography and/or pulse thermography, as disclosed above.

In an alternative non-limiting embodiment, the tissue temperature may be measured 640 by placing a thermochromic liquid crystal material in thermal communication with the tissue, exposing both the tissue and the thermochromic liquid crystal material to a thermal stimulus (either a hot stimulus or a cold stimulus), illuminating the thermochromic liquid crystal material with a source of visible radiation (such as visible radiation having a wavelength of about 380 nm to about 760 nm), and measuring an amount of visible radiation reflected by the thermochromic liquid crystal material by a camera sensitive to visible radiation. In one non-limiting example, the thermochromic liquid crystal material may be placed in thermal communication with the tissue by spraying the thermochromic liquid crystal material on the tissue. Some non-limiting examples of thermochromic liquid crystal material may include one or more of cholesteryl acetate, cholesteryl benzoate, cholesteryl chloride, cholesteryl 2,4-dichlorobenzoate, cholesteryl isostearylcarbonate, cholesteryl p-nitrobenzoate, cholesteryl nonanoate, choesteryl p-nonylphenylcarbonate, cholesteryl oleate, cholesteryl oleylcarbonate, and cholesteryl propionate.

In another non-limiting example, the thermochromic liquid crystal material may be placed in thermal communication with the tissue by applying an encapsulated thermochromic liquid crystal material on the tissue, in which the encapsulating material may be a bio-inert carrier. Non-limiting examples of such bio-inert carrier material may include one or more of alginates, polyacrylamide-coated agarose, polyvinyl alcohol, cellulose sulfate, water insoluble polymethyl methacrylate, polyethylene glycol, and polyacrylonitrile hydrogels.

It may be appreciated that methods that may include the use of thermochromic materials, either alone or in encapsulated form, may also include a step of irrigating the tissue to remove the thermochromic liquid crystal material once the measurements have been completed.

Once the tissue thermal response data have been obtained, an electronic system, as substantially disclosed above, may calculate 650 a comparison between at least one viability threshold value and the tissue response data. The viability threshold value may be determined according to a number of different methods. In one non-limiting example, a viability threshold value may be determined at least in part by obtaining tissue response data of a similar tissue as that being assessed under essentially the same thermal stimulus conditions. As a non-limiting example, the tissue at a bowel resection anastomosis of a patient may be assessed by comparing its response to that of bowel tissue of the same patient at a segment of bowel at some distance from the site of resection. As another non-limiting example, the tissue at a bowel resection anastomosis of a patient may be assessed by comparing its response to that of bowel tissue of a different patient. As yet another non-limiting example, the tissue at a bowel resection anastomosis of a patient may be assessed by comparing its response to that of bowel of a non-human animal that may be considered an adequate model of human bowel perfusion response.

In one non-limiting example, sources for one or more viability threshold values may include values derived from an aggregate or average response of several tissues to at least one thermal stimulus. In another non-limiting example, sources for one or more viability threshold values may include values derived at least in part from one or more mathematical models of predicted tissue response to at least one thermal stimulus.

As disclosed above, a number of metrics may be derived from the response of a tissue to one or more thermal stimuli. These metrics may constitute a single-valued metric. In one non-limiting example, a single-valued metric may constitute an average maximum temperature of a portion of tissue after a thermal stimulus has been removed. Alternatively, the metrics may constitute multi-valued metrics. In one non-limiting example, a multi-valued metric may constitute a time course response of a portion of tissue during a thermal stimulus and after its removal. In another non-limiting example, a multi-valued metric may constitute a maximum temperature of a tissue recorded at several discrete locations after a thermal stimulus has been removed.

Thus, a comparison between the tissue response data and the one or more viability threshold values may be calculated according to a number of methods. In one non-limiting example, calculating 650 a comparison between the response data and the one or more may threshold values may include calculating 650 an absolute difference between them. In one non-limiting example, calculating 650 a comparison between the response data and the one or more threshold values may include calculating a percent difference between them. In another non-limiting example, calculating 650 a comparison between the response data and the one or more threshold values may include calculating an average difference between them. In another non-limiting example, calculating 650 a comparison between the response data and the one or more threshold values may include calculating an average percent difference between them. In yet another non-limiting example, calculating 650 a comparison between the response data and the one or more threshold values may include calculating a difference in a rate of temperature change between the response data and the one or more threshold values. In yet another non-limiting example, calculating 650 a comparison between the response data and the one or more threshold values may include calculating a difference in a thermal recovery time of the tissue to a pre-set temperature. In still another non-limiting example, calculating 650 a comparison between the response data and the one or more threshold values may include calculating a variance measurement between them.

Once the comparison between the tissue response to the one or more thermal stimuli has been compared to the one or more viability threshold values, tissue viability may be determined 660. In one non-limiting embodiment, a tissue assessed by means of its response to thermal stimuli may be determined 660 to be either viable or non-viable. In another non-limiting embodiment, a tissue assessed by means of its response to thermal stimuli may be determined 660 to have a percent likelihood of viability. In another non-limiting embodiment, a tissue assessed by means of its response to thermal stimuli may be determined 660 to be non-viable if the tissue response data is less than about 50% of the viability threshold value. In another non-limiting embodiment, a tissue assessed by means of its response to thermal stimuli may be determined 660 to be non-viable if the tissue response data is less than about 30% of the viability threshold value.

In addition to the results of the determination 660 of tissue viability, raw tissue temperature data, as thermography images, may be presented to a user of the system as well. Thermography images may be interpreted as absolute tissue temperature measurements and may be compared with pre-determined ranges for normal and impaired responses. In one non-limiting embodiment, thermography images may be superimposed over a visual picture of the tissue, and normal and impaired sections of the bowel may be correspondingly color-coded. In another non-limiting embodiment, a series of tissue thermographs may be captured while one or more thermal stimuli are applied to the tissue. The time-varying series of tissue temperature data may then be processed to create a single image that may indicate a distribution of heat transfer rates of the tissue, rather than an absolute temperature of the tissue surface. An image corresponding to such tissue thermal transfer rates may then be superimposed over an image of the tissue. Impaired tissue may be color-coded using a predetermined threshold for normal or impaired heat transfer rates.

While the system and method disclosed above have been described in terms of surgical procedures related to bowel resection, it may be appreciated that such systems and methods may also be useful in other procedures in which reliable tissue viability assessment may be needed. Non-limiting examples of such alternative procedures may include skin flap reconstructive surgery, such as for burn or trauma patients, breast reconstructive surgery after breast tissue resection, cardiac ventricular reconstructive surgery (e.g. a Dor procedure) for treating heart failure, and for evaluating difficult-to-heal wounds.

EXAMPLES

Example 1

A System for Determining Tissue Viability

A system configured for circulating temperature-controlled humidified air or gas over exposed tissue may be used as a source of a thermal stimuli. Blowing temperature-controlled humidified air over the tissue may be useful because it is a simple-to-control method of providing both a warming and a cooling phase of a thermal challenge with a single piece of equipment. It also may have a number of other advantages including easily adjustable air temperature, ability to apply the thermal challenge from a distance, minimal interfere with surgical instruments present in the operating field, the ability to provide the thermal challenge to both front and back portions of the bowel, and ability to permit surgical procedures to additional tissue at a distance from the thermal challenge.

A standard diagnostic infrared camera may be used for thermal imaging purposes. The diagnostic camera may have sufficient geometrical resolution of at least 320×240 detector elements, and have a thermal resolution (sensitivity) less than about 80 mK.

Example 2

A Tissue Thermal Stimulus Protocol

Tissue viability assessment may be conducted at the beginning of surgery, during surgery such as during anastomosis construction or after the bowel resection is complete, and prior to finishing the surgery. Conducting tissue viability assessment several times during the surgery may raise confidence that the remaining intestinal tissue is well perfused at various points during operation, on one or both sides of the anastomosis.

In one non-limiting application of the method, tissue unexposed to a thermal stimulus may first be observed with the thermal imaging camera so as to establish a baseline image. The thermal stimulus, which may include a short period of heating, cooling or combination thereof, may then applied. The tissue response to the stimulus may then be measured. Tissue viability may be determined, at least in part, on a rate of tissue temperature change, an absolute value of tissue temperature determined during a pre-specified period of time, and/or on a time lag between the application of the stimulus and a measured tissue response.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method of assessing tissue viability, the method comprising:
   providing at least one source of thermal stimulation of a tissue, wherein the at least one source of thermal stimulation provides at least one thermal stimulus;
   providing a measurement system for obtaining response data related to at least one response to the at least one thermal stimulus by the tissue;
   applying the at least one thermal stimulus to the tissue, wherein applying the at least one thermal stimulus comprises:
      applying a first thermal stimulus for a first period of time;
      applying a null stimulus for a second period of time, wherein the null stimulus comprises a thermal stimulus at about ambient temperature or at about normal human core temperature; and
      applying a second thermal stimulus for a third period of time;
   measuring, by the measurement system, at least some tissue response data related to a response of the tissue to the at least one thermal stimulus;
   calculating, by an electronic system, a comparison between the tissue response data and at least one viability threshold value; and
   determining, by the electronic system, the tissue viability based at least in part on the comparison.

2. The method of claim 1, wherein applying the at least one thermal stimulus comprises applying a heat stimulus causing the tissue to attain a temperature of about 37° C. to about 42° C.

3. The method of claim 1, wherein applying the at least one thermal stimulus comprises applying a heat stimulus causing the tissue to attain a temperature of about 42° C.

4. The method of claim 1, wherein applying the at least one thermal stimulus comprises applying a cold stimulus causing the tissue to attain a temperature of about 32° C. to about 37° C.

5. The method of claim 1, wherein applying the at least one thermal stimulus comprises applying a cold stimulus causing the tissue to attain a temperature of about 32° C.

6. The method of claim 1, wherein applying the at least one thermal stimulus comprises applying a heat stimulus for a first period of time of about 0.5 minutes to about 5 minutes.

7. The method of claim 1, wherein applying the at least one thermal stimulus comprises applying a heat stimulus for a first period of time of about 1 minute.

8. The method of claim 1, wherein applying the at least one thermal stimulus comprises applying a cold stimulus for a second period of time of about 0.5 minutes to about 5 minutes.

9. The method of claim 1, wherein applying the at least one thermal stimulus comprises applying a cold stimulus for a second period of time of about 1 minute.

10. The method of claim 1, wherein the second period of time is greater than about 0 minutes and less than about 5 minutes.

11. The method of claim 1, wherein measuring by the measurement system comprises measuring an amount of thermal radiation emitted by the tissue by a thermal sensitive camera.

12. The method of claim 1, wherein measuring by the measurement system comprises:
    placing a thermochromic liquid crystal material in thermal communication with the tissue;
    illuminating the thermochromic liquid crystal material with a source of visible radiation; and
    measuring an amount of visible radiation reflected by the thermochromic liquid crystal material by a camera sensitive to the visible radiation.

13. The method of claim 12, wherein providing at least one source of thermal stimulation comprises heating the thermochromic liquid crystal material to a thermal stimulus temperature.

14. The method of claim 12, wherein providing at least one source of thermal stimulation comprises cooling the thermochromic liquid crystal material to a thermal stimulus temperature.

15. The method of claim 12, wherein placing the thermochromic liquid crystal material in thermal communication with the tissue comprises spraying the thermochromic liquid crystal material on the tissue.

16. The method of claim 12, wherein placing the thermochromic liquid crystal material in thermal communication with the tissue comprises applying an encapsulated thermochromic liquid crystal material on the tissue.

17. The method of claim 16, wherein the encapsulated thermochromic liquid crystal material comprises a thermochromic liquid crystal material encapsulated in a bio-inert carrier.

18. The method of claim 17, wherein the bio-inert carrier comprises one or more of the following: alginates, polyacrylamide-coated agarose, polyvinyl alcohol, cellulose sulfate, water insoluble polymethyl methacrylate, polyethylene glycol, and polyacrylonitrile hydrogels.

19. The method of claim 12, wherein the thermochromic liquid crystal material comprises one or more of the following: cholesteryl acetate, cholesteryl benzoate, cholesteryl chloride, cholesteryl 2,4-dichlorobenzoate, cholesteryl isostearylcarbonate, cholesteryl p-nitrobenzoate, cholesteryl nonanoate, choesteryl p-nonylphenylcarbonate, cholesteryl oleate, cholesteryl oleylcarbonate, and cholesteryl propionate.

20. The method of claim 12 further comprising irrigating the tissue to remove the thermochromic liquid crystal material.

21. The method of claim 12, wherein visible radiation comprises radiation having a wavelength of about 380 nm to about 760 nm.

22. The method of claim 1, wherein measuring at least some tissue response data comprises using infrared lock-in thermography, pulse thermography, or a combination thereof.

23. The method of claim 1, wherein the tissue response data comprises one or more of the following: a single temperature of the tissue, an average temperature of the tissue over a period of time, a maximum temperature of the tissue, and a plurality of temperature measurements of the tissue over a period of time.

24. The method of claim 1, wherein the tissue is a tissue type, and the viability threshold value is determined at least in part by a response of a second tissue of the tissue type to at least one thermal stimulus.

25. The method of claim 24, wherein the tissue is from an animal source, and the second tissue is from the animal source.

26. The method of claim 24, wherein the tissue is from a first animal source of a species, and the second tissue is from a second animal source of the species.

27. The method of claim 24, wherein the tissue is from a first animal source of a first species, and the second tissue is from a second animal source of a second species.

28. The method of claim 1, wherein the viability threshold value is determined at least in part from an aggregate response of a plurality of tissues to at least one thermal stimulus.

29. The method of claim 1, wherein the viability threshold value is determined at least in part from a mathematical model of a response of a tissue to at least one thermal stimulus.

30. The method of claim 1, wherein calculating a comparison comprises one or more of the following: calculating an absolute difference, calculating a percent difference, calculating an average difference, calculating an average percent difference, calculating a difference in a rate of temperature change, calculating a difference in a thermal recovery time of the tissue to a pre-set temperature, and calculating a variance measurement.

31. The method of claim 1, wherein determining the tissue viability comprises determining that the comparison of the tissue response data to the viability threshold value is less than about 50%.

32. The method of claim 1, wherein determining the tissue viability comprises determining that the comparison of the tissue response data to the viability threshold value is less than about 30%.

33. The method of claim 1, wherein the at least one thermal stimulus comprises a heated or cooled gas.

34. The method of claim 1, wherein the at least one thermal stimulus comprises temperature-controlled humidified air.

* * * * *